United States Patent
Mazanec

(10) Patent No.: US 11,839,765 B2
(45) Date of Patent: Dec. 12, 2023

(54) COCHLEAR IMPLANT SYSTEM WITH INTEGRATED SIGNAL ANALYSIS FUNCTIONALITY

(71) Applicant: Envoy Medical Corporation, White Bear Lake, MN (US)

(72) Inventor: Paul R. Mazanec, Ham Lake, MN (US)

(73) Assignee: Envoy Medical Corporation, White Bear Lake, MN (US)

( * ) Notice: Subject to any disclaimer, the term of this patent is extended or adjusted under 35 U.S.C. 154(b) by 334 days.

(21) Appl. No.: 17/182,477

(22) Filed: Feb. 23, 2021

(65) Prior Publication Data

US 2022/0266038 A1 Aug. 25, 2022

(51) Int. Cl.
*A61N 1/36* (2006.01)
*H04R 25/00* (2006.01)
(Continued)

(52) U.S. Cl.
CPC ....... *A61N 1/36038* (2017.08); *A61N 1/0541* (2013.01); *A61N 1/378* (2013.01);
(Continued)

(58) Field of Classification Search
CPC .............. A61N 1/36038; A61N 1/0541; A61N 1/37223; A61N 1/37247; A61N 1/378;
(Continued)

(56) References Cited

U.S. PATENT DOCUMENTS

| 2,827,041 A | 3/1958 | Pierson |
| 4,400,590 A | 8/1983 | Michelson |

(Continued)

FOREIGN PATENT DOCUMENTS

| CN | 104394930 A | 3/2015 |
| CN | 10086237 A | 8/2019 |

(Continued)

OTHER PUBLICATIONS

PCT International Search Report and Written Opinion dated May 25, 2022 for related Intl. App. No. PCT/US2022/017140, 9 pgs.

(Continued)

*Primary Examiner* — Catherine M Voorhees
(74) *Attorney, Agent, or Firm* — Fredrikson & Byron, P.A.

(57) ABSTRACT

A cochlear implant and analysis system includes a stimulator, an input source, a signal processor, a wireless communication interface, and an external device. The system can receive an acoustic stimulus, generate an input signal representative thereof, and apply a transfer function to the input signal to generate and output a stimulation signal to the stimulator. The signal processor can receive an analysis input indicating a first signal for analysis and generate an analysis signal based on the received analysis input. The first signal can be an input signal from an input source or a result of one or more processing steps. The signal processor can output the analysis signal to the wireless communication interface with the wireless communication interface configured to output a signal representative of the analysis signal to an external device.

22 Claims, 10 Drawing Sheets

(51) Int. Cl.
*A61N 1/05* (2006.01)
*A61N 1/372* (2006.01)
*A61N 1/378* (2006.01)

(52) U.S. Cl.
CPC ..... *A61N 1/37223* (2013.01); *A61N 1/37247* (2013.01); *H04R 25/305* (2013.01); *H04R 25/505* (2013.01); *H04R 25/554* (2013.01); *H04R 25/602* (2013.01); *H04R 25/609* (2019.05); *A61N 1/37241* (2013.01); *H04R 2225/55* (2013.01); *H04R 2225/67* (2013.01)

(58) Field of Classification Search
CPC .............. A61N 1/37241; H04R 25/305; H04R 25/505; H04R 25/554; H04R 25/602; H04R 25/609; H04R 2225/55; H04R 2225/67
See application file for complete search history.

(56) References Cited

U.S. PATENT DOCUMENTS

| | | |
|---|---|---|
| 4,495,384 A | 1/1985 | Scott et al. |
| 4,729,366 A | 3/1988 | Schaefer |
| 4,850,962 A | 7/1989 | Schaefer |
| 4,918,745 A | 4/1990 | Hutchison |
| 5,540,095 A | 7/1996 | Sherman et al. |
| 5,762,583 A | 6/1998 | Adams et al. |
| 6,195,585 B1 | 2/2001 | Karunasiri et al. |
| 6,212,431 B1 | 4/2001 | Hahn et al. |
| 6,259,951 B1 | 7/2001 | Kuzma et al. |
| 6,272,382 B1 | 8/2001 | Faltys et al. |
| 6,308,101 B1 | 10/2001 | Faltys et al. |
| 6,358,281 B1 | 3/2002 | Berrang et al. |
| 7,225,028 B2 | 5/2007 | Della Santina et al. |
| 7,319,906 B2 | 1/2008 | Kuzma et al. |
| 7,376,563 B2 | 5/2008 | Leysieffer et al. |
| 7,524,278 B2 | 4/2009 | Madsen et al. |
| 7,864,968 B2 | 1/2011 | Kulkarni et al. |
| 7,916,823 B1 | 3/2011 | Hartley |
| 3,170,677 A1 | 5/2012 | Chambers et al. |
| 8,503,685 B2 | 8/2013 | Kulkarni et al. |
| 8,554,329 B1 | 10/2013 | Mann et al. |
| 8,655,449 B2 | 2/2014 | Haller et al. |
| 9,205,272 B2 | 12/2015 | Suaning et al. |
| 9,504,076 B2 | 11/2016 | El-Hoiydi et al. |
| 9,539,430 B2 | 1/2017 | Mishra et al. |
| 9,716,952 B2 | 7/2017 | Mauger |
| 2002/0039425 A1 | 4/2002 | Burnett et al. |
| 2002/0099421 A1 | 7/2002 | Goldsmith et al. |
| 2004/0230254 A1 | 11/2004 | Harrison et al. |
| 2005/0033384 A1 | 2/2005 | Sacha |
| 2005/0197677 A1 | 9/2005 | Stevenson |
| 2006/0122664 A1 | 6/2006 | Sacha et al. |
| 2006/0183965 A1 | 8/2006 | Kasic, II et al. |
| 2008/0195179 A1 | 8/2008 | Quick |
| 2008/0300658 A1 | 12/2008 | Meskens |
| 2009/0018616 A1 | 1/2009 | Quick et al. |
| 2009/0082831 A1 | 3/2009 | Paul et al. |
| 2009/0187233 A1 | 7/2009 | Stracener |
| 2009/0192565 A1 | 7/2009 | Lee et al. |
| 2010/0030012 A1* | 2/2010 | Meskens .............. H04R 25/554 607/57 |
| 2010/0042183 A1 | 2/2010 | Beck |
| 2010/0317913 A1 | 12/2010 | Conn et al. |
| 2011/0082521 A1 | 4/2011 | Botros et al. |
| 2011/0116669 A1 | 5/2011 | Karunasiri |
| 2011/0137180 A1 | 6/2011 | Johnson et al. |
| 2011/0144719 A1 | 6/2011 | Perkins et al. |
| 2011/0160808 A1 | 6/2011 | Lyden et al. |
| 2011/0280426 A1 | 11/2011 | Bachler |
| 2011/0295331 A1 | 12/2011 | Wells et al. |
| 2012/0063610 A1* | 3/2012 | Kaulberg .............. H04R 25/407 381/71.1 |
| 2012/0215285 A1 | 8/2012 | Tahmasian et al. |
| 2012/0277835 A1 | 11/2012 | Della Santina et al. |
| 2013/0018216 A1 | 1/2013 | Beckerle et al. |
| 2013/0023953 A1 | 1/2013 | van den Honert |
| 2013/0193914 A1 | 8/2013 | Gaddam et al. |
| 2013/0223664 A1 | 8/2013 | Meskens et al. |
| 2013/0238055 A1 | 9/2013 | Marnfeldt et al. |
| 2013/0268025 A1 | 10/2013 | Ranu |
| 2013/0278226 A1 | 10/2013 | Cong et al. |
| 2013/0317584 A1 | 11/2013 | Stevenson et al. |
| 2014/0058482 A1 | 2/2014 | Gupta et al. |
| 2014/0155947 A1 | 6/2014 | Kroll et al. |
| 2014/0247954 A1 | 9/2014 | Hall et al. |
| 2014/0270211 A1 | 9/2014 | Solum et al. |
| 2014/0275730 A1 | 9/2014 | Lievens et al. |
| 2014/0309712 A1 | 10/2014 | Masaki et al. |
| 2014/0350652 A1 | 11/2014 | Suwito |
| 2015/0125012 A1 | 5/2015 | Sabin |
| 2015/0174416 A1 | 6/2015 | Angara et al. |
| 2015/0224312 A1 | 8/2015 | Platz et al. |
| 2015/0256945 A1 | 9/2015 | Mazanec |
| 2015/0374988 A1 | 12/2015 | Laudanski |
| 2015/0375003 A1 | 12/2015 | Meskens |
| 2016/0050500 A1* | 2/2016 | Liao ..................... H04R 25/552 381/23.1 |
| 2016/0227333 A1 | 8/2016 | Babico |
| 2017/0043162 A1 | 2/2017 | Lopez-Poveda |
| 2017/0077938 A1 | 3/2017 | Heubi |
| 2017/0094396 A1 | 3/2017 | Chandramohan et al. |
| 2017/0161449 A1 | 6/2017 | Meskens |
| 2017/0259072 A1 | 9/2017 | Newham et al. |
| 2017/0360364 A1 | 12/2017 | Heasman et al. |
| 2018/0028811 A1 | 2/2018 | Van Gerwen et al. |
| 2018/0028827 A1 | 2/2018 | Schilling et al. |
| 2018/0041848 A1 | 2/2018 | Nielsen et al. |
| 2018/0050197 A1 | 2/2018 | Mazanec et al. |
| 2018/0050198 A1 | 2/2018 | Mazanec et al. |
| 2018/0050203 A1* | 2/2018 | Mazanec ............ A61N 1/36128 |
| 2018/0059870 A1 | 3/2018 | Krah |
| 2018/0264269 A1 | 9/2018 | Meadows |
| 2018/0317027 A1 | 11/2018 | Bolner et al. |
| 2018/0333577 A1 | 11/2018 | Nygard et al. |
| 2018/0361151 A1 | 12/2018 | Ridler et al. |
| 2019/0045308 A1 | 2/2019 | Chen et al. |
| 2019/0046116 A1 | 2/2019 | Shah et al. |
| 2019/0344073 A1* | 11/2019 | Baker ................. A61N 1/37247 |
| 2020/0054877 A1 | 2/2020 | Calixto et al. |
| 2020/0238075 A1 | 7/2020 | Mazanec et al. |
| 2020/0269034 A1 | 8/2020 | Mazanec et al. |
| 2020/0269035 A1 | 8/2020 | Mazanec et al. |
| 2020/0269047 A1 | 8/2020 | Mazanec et al. |
| 2020/0269048 A1 | 8/2020 | Mazanec et al. |
| 2020/0269057 A1 | 8/2020 | Mazanec et al. |
| 2020/0269058 A1 | 8/2020 | Mazanec et al. |
| 2021/0084417 A1 | 3/2021 | Bagazov et al. |
| 2021/0135704 A1 | 5/2021 | El-Hoiydi et al. |
| 2021/0187293 A1 | 6/2021 | Friedling |
| 2021/0361194 A1 | 11/2021 | Arab et al. |
| 2022/0339445 A1* | 10/2022 | Litvak ................ A61N 1/36039 |

FOREIGN PATENT DOCUMENTS

| | | |
|---|---|---|
| DE | 4419070 A1 | 12/1994 |
| DE | 60107062 T2 | 11/2005 |
| DE | 102013214049 B4 | 3/2015 |
| EP | 1043914 A2 | 10/2000 |
| EP | 1683544 B1 | 11/2010 |
| EP | 2884766 B1 | 2/2018 |
| EP | 3120579 B1 | 2/2020 |
| TW | 201142830 A | 12/2011 |
| WO | 2007137032 A2 | 11/2007 |
| WO | 2010056768 A1 | 5/2010 |
| WO | 2014037888 A1 | 3/2014 |
| WO | 2015077773 A1 | 5/2014 |
| WO | 2016122606 A1 | 8/2016 |
| WO | 2017100866 A1 | 6/2017 |
| WO | 2018035329 A1 | 2/2018 |

(56) References Cited

FOREIGN PATENT DOCUMENTS

WO     2018144732 A1     8/2018
WO     2020172500 A1     8/2020

OTHER PUBLICATIONS

Mazanec et al., Unpublished U.S. Appl. No. 17/006,467, entitled Programming of Cochlear Implant Accessories, filed Aug. 28, 2020, 74 pages.
Mazanec et al., Unpublished U.S. Appl. No. 17/109,303, entitled Implantable Cochlear System With Inner Ear Sensor, filed Dec. 2, 2020, 54 pages.
Mazanec et al., Unpublished U.S. Appl. No. 17/109,304, entitled Combination Hearing Aid and Cochlear Implant System, filed Dec. 2, 2020, 55 pages.
Mazanec et al., Unpublished U.S. Appl. No. 17/109,305, entitled Cochlear Implant Stimulation Calibration, filed Dec. 2, 2020, 53 pages.

\* cited by examiner

COCHLEAR IMPLANT SYSTEM WITH INTEGRATED SIGNAL ANALYSIS FUNCTIONALITY

BACKGROUND

A cochlear implant is an electronic device that may be at least partially implanted surgically into the cochlea, the hearing organ of the inner ear, to provide improved hearing to a patient. Cochlear implants may include components that are worn externally by the patient and components that are implanted internally in the patient. Implant system can receive acoustic stimuli and output electrical stimuli in response thereto. However, because various components may be fully implanted, operation of such implanted components may be difficult to test, and system operation issues may be difficult to diagnose.

SUMMARY

Some aspects of the disclosure include cochlear implant and analysis systems. Such systems can include a cochlear electrode, a stimulator in electrical communication with the cochlear electrode, an input source, and a signal processor. The signal processor can be configured to receive an input signal from the input source and output a stimulation signal to the stimulator based on the received input signal and a transfer function of the signal processor.

The implantable cochlear implant system can include a wireless communication interface. Additionally, the signal processor of the implantable cochlear implant system can be configured to receive an analysis input indicating a first signal for analysis. The first signal for analysis can comprise the input signal or a result of one or more processing steps performed by the signal processor, such as a stimulation signal. The signal processor can be further configured to generate an analysis signal based on the received analysis input with the analysis signal comprising a representation of the first signal. Further, the signal processor can be configured to output the analysis signal to the wireless communication interface, whereby the wireless communication interface is configured to output a signal representative of the analysis signal to an external device.

In various examples, the analysis signal can be the first signal itself, a downsampled version thereof, or a transformed version of the first signal, such as a frequency domain representation thereof. In some examples, the wireless communication interface is configured to stream the analysis signal to the external device. In some examples, the wireless communication interface is configured to downsample or otherwise modify the analysis signal to output a signal representative thereof.

In some examples, the external device includes a speaker and/or display. The external device can be configured to output an audible and/or visible representation of the analysis signal.

DETAILED DESCRIPTION

Figure 1:
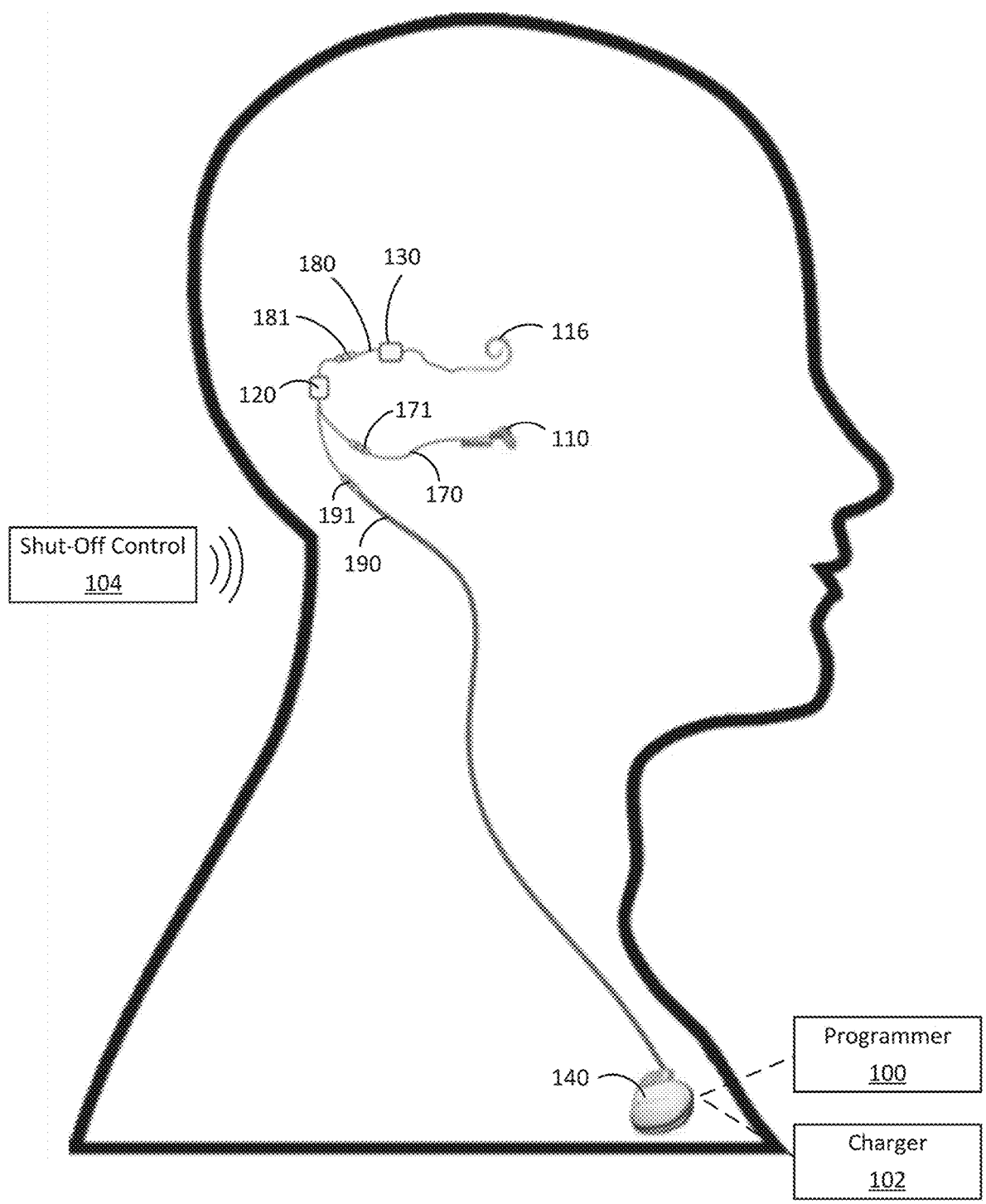
FIG. 1 shows a schematic illustration of a fully implantable cochlear implant system.

FIG. 1 shows a schematic illustration of a fully implantable cochlear implant system. The system of FIG. 1 includes a middle ear sensor 110 in communication with a signal processor 120. The middle ear sensor 110 can be configured to detect incoming sound waves, for example, using the ear structure of a patient. The signal processor 120 can be configured to receive a signal from the middle ear sensor 110 and produce an output signal based thereon. For example, the signal processor 120 can be programmed with instructions to output a certain signal based on a received signal. In some embodiments, the output of the signal processor 120 can be calculated using an equation based on received input signals. Alternatively, in some embodiments, the output of the signal processor 120 can be based on a lookup table or other programmed (e.g., in memory) correspondence between the input signal from the middle ear sensor 110 and the output signal. While not necessarily based explicitly on a function, the relationship between the input to the signal processor 120 (e.g., from the middle ear sensor 110) and the output of the signal processor 120 is referred to as the transfer function of the signal processor 120.

In various examples, the signal processor 120 can comprise any variety of components, for example, digital and/or analog processing components. In some embodiments, signal processor 120 comprises a digital signal processor, one or more microprocessors, microcontrollers, application specific integrated circuits (ASICs) or the like. Supporting circuitry for one or more such components can also be included as a part of the signal processor. In some embodiments, the signal processor can include or otherwise communicate with a memory containing programming for operating one or more components. Additionally or alternatively, in some embodiments, the signal processor can include one or more additional components. For example, in some embodiments, signal processor can include an embedded microphone or other sensor configured to detect incoming sound waves.

The system of FIG. 1 further includes a cochlear electrode 116 implanted into the cochlear tissues of a patient. The cochlear electrode 116 is in electrical communication with an electrical stimulator 130, which can be configured to provide electrical signals to the cochlear electrode 116 in response to input signals received by the electrical stimulator 130. In some examples, the cochlear electrode 116 is fixedly attached to the electrical stimulator 130. In other examples, the cochlear electrode 116 is removably attached to the electrical stimulator 130. As shown, the electrical stimulator 130 is in communication with the signal processor 120. In some embodiments, the electrical stimulator 130 provides electrical signals to the cochlear electrode 116 based on output signals from the signal processor 120.

In various embodiments, the cochlear electrode 116 can include any number of contact electrodes in electrical contact with different parts of the cochlear tissue. In such embodiments, the electrical stimulator 130 can be configured to provide electrical signals to any number of such contact electrodes to stimulate the cochlear tissue. For example, in some embodiments, the electrical stimulator 130 is configured to activate different contact electrodes or combinations of contact electrodes of the cochlear electrode 116 in response to different input signals received from the signal processor 120. This can help the patient differentiate between different input signals.

During exemplary operation, the middle ear sensor 110 detects audio signals, for example, using features of the patient's ear anatomy as described elsewhere herein and in U.S. Patent Publication No. 2013/0018216, which is hereby incorporated by reference in its entirety. The signal processor 120 can receive such signals from the middle ear sensor 110 and produce an output to the electrical stimulator 130 based on the transfer function of the signal processor 120. The electrical stimulator 130 can then stimulate one or more contact electrodes of the cochlear electrode 116 based on the received signals from the signal processor 120.

Figure 2:
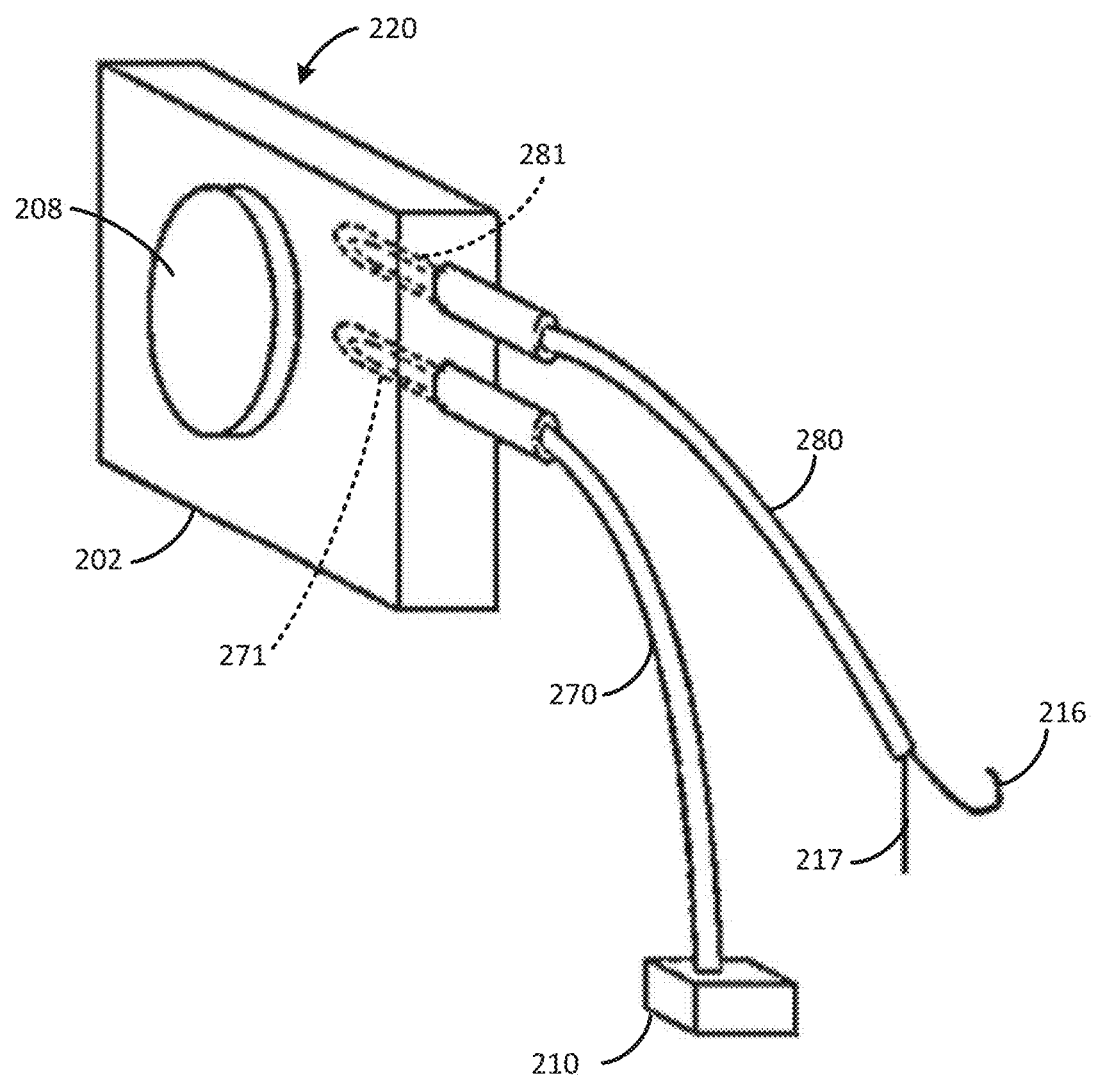
FIG. 2 shows an embodiment of a fully-implantable cochlear implant.

Referring to FIG. 2, an embodiment of a fully-implantable cochlear implant is shown. The device in this embodiment includes a processor 220 (e.g., signal processor), a sensor 210, a first lead 270 connecting the sensor 210 to the processor 220, and a combination lead 280 attached to the processor 220, wherein combination lead 280 contains both a ground electrode 217 and a cochlear electrode 216. The illustrated processor 220 includes a housing 202, a coil 208, first female receptacle 271 and second female receptacle 281 for insertion of the leads 270 and 280, respectively.

In some embodiments, coil 208 can receive power and/or data from an external device, for instance, including a transmission coil (not shown). Some such examples are described in U.S. Patent Publication No. 2013/0018216, which is incorporated by reference. In other examples, processor 220 is configured to receive power and/or data from other sources, such as an implantable battery and/or communication module as shown in FIG. 1. Such battery and/or communication module can be implanted, for example, into the pectoral region of the patient in order to provide adequate room for larger equipment (e.g., a relatively large battery) for prolonged operation (e.g., longer battery life). Additionally, in the event a battery needs eventual replacement, a replacement procedure in the patient's pectoral region can be performed several times without certain vascularization issues that can arise near the location of the cochlear implant. For example, in some cases, repeated procedures (e.g., battery replacement) near the cochlear implant can result in a decreased ability for the skin in the region to heal after a procedure. Placing a replaceable component such as a battery in the pectoral region can facilitate replacement procedures with reduced risk for such issues.

Figure 3:
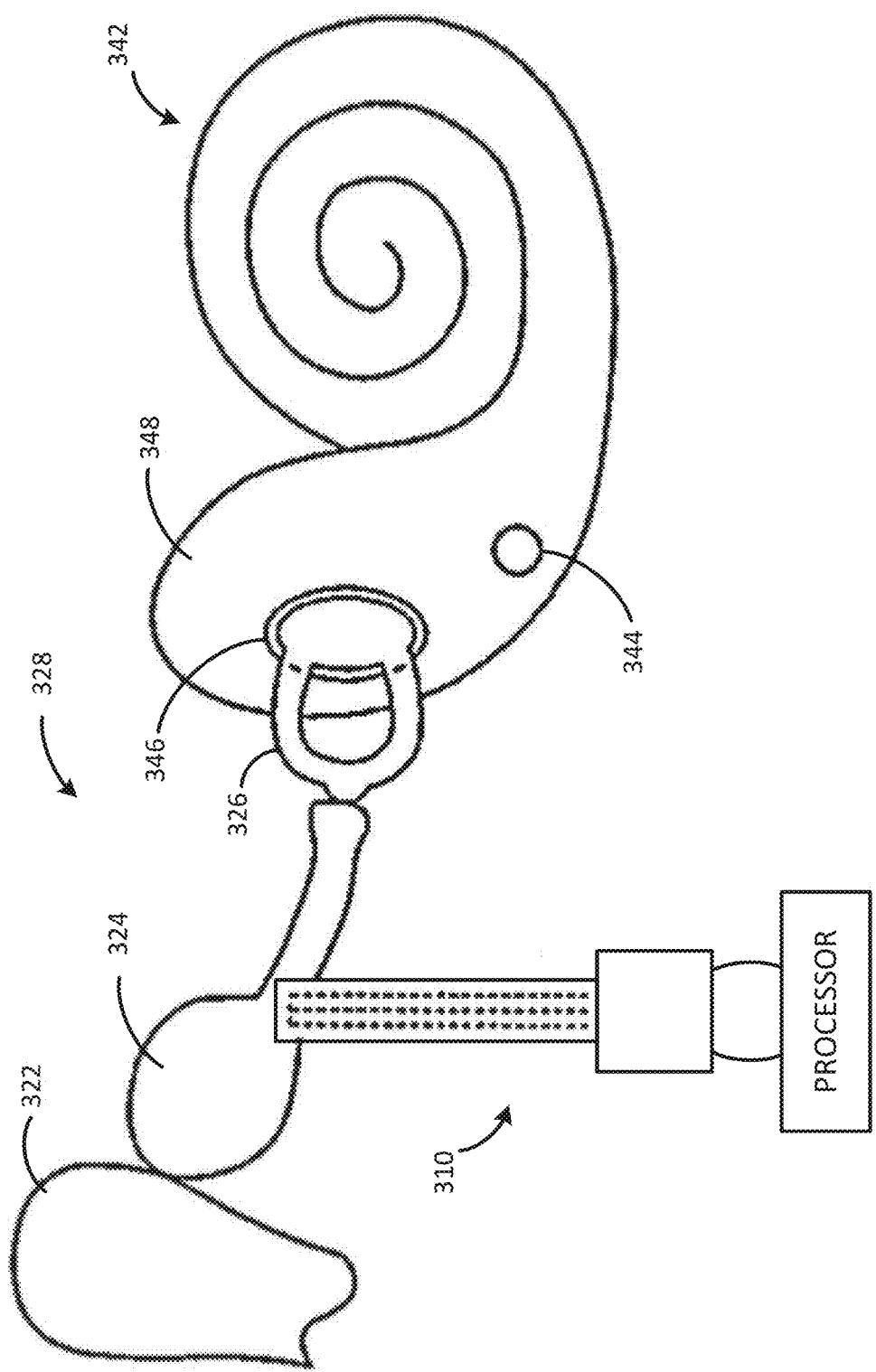
FIG. 3 illustrates an embodiment of an exemplary middle ear sensor for use in conjunction with anatomical features of a patient.

FIG. 3 illustrates embodiments of an exemplary middle ear sensor for use in conjunction with anatomical features of a patient. Referring to FIG. 3, an embodiment of the sensor 310 of a fully-implantable cochlear implant is shown. Also shown are portions of the subject's anatomy, which includes, if the subject is anatomically normal, at least the malleus 322, incus 324, and stapes 326 of the middle ear 328, and the cochlea 348, oval window 346, and round window 344 of the inner ear 342. Here, the sensor 310 is touching the incus 324. The sensor 310 can include a sensor such as described in U.S. Patent Publication No. 2013/0018216, which is incorporated by reference. Further, although not shown in a drawing, the sensor 310 may be in operative contact with the tympanic membrane or the stapes, or any combination of the tympanic membrane, malleus 322, incus 324, or stapes 326.

FIG. 3 illustrates an exemplary middle ear sensor for use with systems described herein. However, other middle ear sensors can be used, such as sensors using microphones or other sensors capable of receiving an input corresponding to detected sound and outputting a corresponding signal to the signal processor. Additionally or alternatively, systems can include other sensors configured to output a signal representative of sound received at or near a user's ear, such as a microphone or other acoustic pickup located in the user's outer ear or implanted under the user's skin. Such devices may function as an input source, for example, to the signal processor such that the signal processor receives an input signal from the input source and generates and output one or more stimulation signals according to the received input signal and the signal processor transfer function. Additionally or alternatively, systems can include other types of sensors, such as inner ear sensors. Some example configurations of such systems and other sensor arrangements are described in PCT patent application No. PCT/US20/19166, filed Feb. 21, 2020, which is assigned to the assignee of the instant application and is incorporated by reference.

Referring back to FIG. 1, the signal processor 120 is shown as being in communication with the middle ear sensor 110, the electrical stimulator 130, and the implantable battery and/or communication module 140. As described elsewhere herein, the signal processor 120 can receive input signals from the middle ear sensor 110 and/or other input source(s) and output signals to the electrical stimulator 130 for stimulating the cochlear electrode 116. The signal processor 120 can receive data (e.g., processing data establishing or updating the transfer function of the signal processor 120) and/or power from the implantable battery and/or communication module 140.

In some embodiments, the implantable battery and/or communication module 140 can communicate with one or more external components, such as a programmer 100 and/or a battery charger 102. The battery charger 102 can wirelessly charge the battery in the implantable battery and/or communication module 140 when brought into proximity with the implantable battery and/or communication module 140 in the pectoral region of the patient. Such charging can be accomplished, for example, using inductive charging. The programmer 100 can be configured to wirelessly communicate with the implantable battery and/or communication module 140 via any appropriate wireless communication technology, such as Bluetooth, Wi-Fi, and the like. In some examples, the programmer 100 can be used to update the system firmware and/or software. In an exemplary operation, the programmer 100 can be used to communicate an updated signal processor 120 transfer function to the implantable battery and/or communication module 140. In various embodiments, the programmer 100 and charger 102 can be separate devices or can be integrated into a single device.

In the illustrated example of FIG. 1, the signal processor 120 is connected to the middle ear sensor 110 via lead 170. In some embodiments, lead 170 can provide communication between the signal processor 120 and the middle ear sensor 110. In some embodiments, lead 170 can include a plurality of isolated conductors providing a plurality of communication channels between the middle ear sensor 110 and the signal processor 120. The lead 170 can include a coating such as an electrically insulating sheath to minimize any conduction of electrical signals to the body of the patient. In various embodiments, one or more communication leads can be detachable such that communication between two components can be disconnected in order to electrically and/or mechanically separate such components. For instance, in some embodiments, lead 170 includes a detachable connector 171. Detachable connector 171 can facilitate decoupling of the signal processor 120 and middle ear sensor 110. Example detachable connectors are described in PCT patent application No. PCT/US20/19166, which is incorporated by reference. For example, with reference to FIG. 1, in some embodiments, lead 170 can include a first lead extending from the middle ear sensor 110 having one of a male or a female connector and a second lead extending from the signal processor 120 having the other of the male or female connector. The first and second leads can be connected at detachable connector 171 in order to facilitate communication between the middle ear sensor 110 and the signal processor 120.

In other examples, a part of the detachable connector 171 can be integrated into one of the middle ear sensor 110 and the signal processor 120. For example, in an exemplary embodiment, the signal processor 120 can include a female connector integrated into a housing of the signal processor 120. Lead 170 can extend fully from the middle ear sensor 110 and terminate at a corresponding male connector for inserting into the female connector of the signal processor 120. In still further embodiments, a lead (e.g., 170) can include connectors on each end configured to detachably connect with connectors integrated into each of the components in communication. For example, lead 170 can include two male connectors, two female connectors, or one male and one female connector for detachably connecting with corresponding connectors integral to the middle ear sensor 110 and the signal processor 120. Thus, lead 170 may include two or more detachable connectors.

Similar communication configurations can be established for detachable connector 181 of lead 180 facilitating communication between the signal processor 120 and the stimulator 130 and for detachable connector 191 of lead 190 facilitating communication between the signal processor 120 and the implantable battery and/or communication module 140. Leads (170, 180, 190) can include pairs of leads having corresponding connectors extending from each piece of communicating equipment, or connectors can be built in to any one or more communicating components.

In such configurations, each of the electrical stimulator 130, signal processor 120, middle ear sensor 110, and battery and/or communication module can each be enclosed in a housing, such as a hermetically sealed housing comprising biocompatible materials. Such components can include feedthroughs providing communication to internal components enclosed in the housing. Feedthroughs can provide electrical communication to the component via leads extending from the housing and/or connectors integrated into the components.

In a module configuration such as that shown in FIG. 1, various components can be accessed (e.g., for upgrades, repair, replacement, etc.) individually from other components. For example, as signal processor 120 technology improves (e.g., improvements in size, processing speed, power consumption, etc.), the signal processor 120 implanted as part of the system can be removed and replaced independently of other components. In an exemplary procedure, an implanted signal processor 120 can be disconnected from the electrical stimulator 130 by disconnecting detachable connector 181, from the middle ear sensor 110 by disconnecting detachable connector 171, and from the implantable battery and/or communication module 140 by disconnecting detachable connector 191. Thus, the signal processor 120 can be removed from the patient while other components such as the electrical stimulator 130, cochlear electrode 116, middle ear sensor 110, and battery and/or communication module can remain in place in the patient.

After the old signal processor is removed, a new signal processor can be connected to the electrical stimulator 130, middle ear sensor 110, and implantable battery and/or communication module 140 via detachable connectors 181, 171, and 191, respectively. Thus, the signal processor (e.g., 120) can be replaced, repaired, upgraded, or any combination thereof, without affecting the other system components. This can reduce, among other things, the risk, complexity, duration, and recovery time of such a procedure. In particular, the cochlear electrode 116 can be left in place in the patient's cochlea while other system components can be adjusted, reducing trauma to the patient's cochlear tissue.

Such modularity of system components can be particularly advantageous when replacing a signal processor 120, such as described above. Processor technology continues to improve and will likely continue to markedly improve in the future, making the signal processor 120 a likely candidate for significant upgrades and/or replacement during the patient's lifetime. Additionally, in embodiments such as the embodiment shown in FIG. 1, the signal processor 120 communicates with many system components. For example, as shown, the signal processor 120 is in communication with each of the electrical stimulator 130, the middle ear sensor 110, and the implantable battery and/or communication module 140. Detachably connecting such components with the signal processor 120 (e.g., via detachable connectors 181, 171, and 191) enables replacement of the signal processor 120 without disturbing any other components. Thus, in the event of an available signal processor 120 upgrade and/or a failure of the signal processor 120, the signal processor 120 can be disconnected from other system components and removed.

While many advantages exist for a replaceable signal processor 120, the modularity of other system components can be similarly advantageous, for example, for upgrading any system component. Similarly, if a system component (e.g., the middle ear sensor 110) should fail, the component can be disconnected from the rest of the system (e.g., via detachable connector 171) and replaced without disturbing the remaining system components. In another example, even a rechargeable battery included in the implantable battery and/or communication module 140 may eventually wear out and need replacement. The implantable battery and/or communication module 140 can be replaced or accessed (e.g., for replacing the battery) without disturbing other system components. Further, as discussed elsewhere herein, when the implantable battery and/or communication module 140 is implanted in the pectoral region of the patient, such as in the illustrated example, such a procedure can leave the patient's head untouched, eliminating unnecessarily frequent access beneath the skin.

While various components are described herein as being detachable, in various embodiments, one or more components configured to communicate with one another can be integrated into a single housing. For example, in some embodiments, signal processor 120 can be integrally formed with the stimulator 130 and cochlear electrode 116. For example, in an exemplary embodiment, processing and stimulation circuitry of a signal processor 120 and stimulator 130 can be integrally formed as a single unit in a housing coupled to a cochlear electrode. Cochlear electrode and the signal processor/stimulator can be implanted during an initial procedure and operate as a single unit.

In some embodiments, while the integral signal processor/stimulator/cochlear electrode component does not get removed from a patient due to potential damage to the cochlear tissue into which the cochlear electrode is implanted, system upgrades are still possible. For example, in some embodiments, a modular signal processor may be implanted alongside the integral signal processor/stimulator component and communicate therewith. In some such examples, the integral signal processor may include a built-in bypass to allow a later-implanted signal processor to interface directly with the stimulator. Additionally or alternatively, the modular signal processor can communicate with the integral signal processor, which may be programmed with a unity transfer function. Thus, in some such embodiments, signals from the modular signal processor may be essentially passed through the integral signal processor unchanged so that the modular signal processor effectively controls action of the integral stimulator. Thus, in various embodiments, hardware and/or software solutions exist for upgrading an integrally attached signal processor that may be difficult or dangerous to remove.

While often described herein as using an electrical stimulator to stimulate the patient's cochlear tissue via a cochlear electrode, in some examples, the system can additionally or alternatively include an acoustic stimulator. An acoustic stimulator can include, for example, a transducer (e.g., a piezoelectric transducer) configured to provide mechanical stimulation to the patient's ear structure. In an exemplary embodiment, the acoustic stimulator can be configured to stimulate one or more portions of the patient's ossicular chain via amplified vibrations. Acoustic stimulators can include any appropriate acoustic stimulators, such as those found in the ESTEEM™ implant (Envoy Medical Corp., St. Paul, Minn.) or as described in U.S. Pat. Nos. 4,729,366, 4,850,962, and 7,524,278, and U.S. Patent Publication No. 20100042183, each of which is incorporated herein by reference in its entirety.

Figure 4:
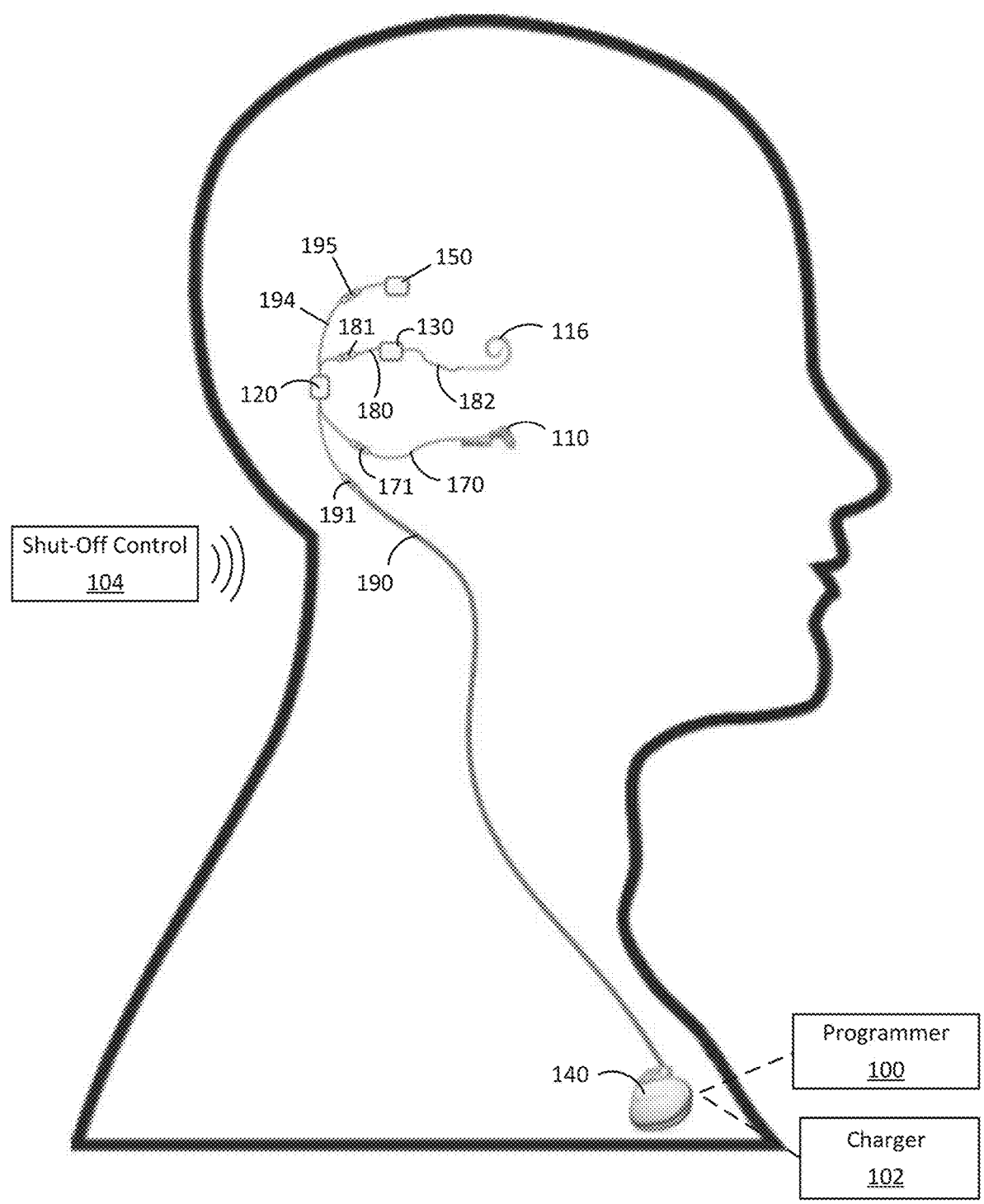
FIG. 4 is a schematic diagram illustrating an exemplary implantable system including an acoustic stimulator.

FIG. 4 is a schematic diagram illustrating an exemplary implantable system including an acoustic stimulator. The acoustic stimulator can be implanted proximate the patient's ossicular chain and can be in communication with a signal processor via lead 194 and detachable connector 195. The signal processor can behave as described elsewhere herein and can be configured to cause acoustic stimulation of the ossicular chain via the acoustic stimulator in in response to input signals from the middle ear sensor according to a transfer function of the signal processor.

The acoustic stimulator of FIG. 4 can be used similarly to the electrical stimulator as described elsewhere herein. For instance, an acoustic stimulator can be mechanically coupled to a patient's ossicular chain upon implanting the system and coupled to the signal processor via lead 194 and detachable connector 195. Similarly to systems described elsewhere herein with respect to the electrical stimulator, if the signal processor requires replacement or repair, the signal processor can be disconnected from the acoustic stimulator (via detachable connector 195) so that the signal processor can be removed without disturbing the acoustic stimulator.

In general, systems incorporating an acoustic stimulator such as shown in FIG. 4 can operate in the same way as systems described elsewhere herein employing an electrical stimulator and cochlear electrode only substituting electrical stimulation for acoustic stimulation.

Some systems can include a hybrid system comprising both an electrical stimulator and an acoustic stimulator in communication with the signal processor. In some such examples, the signal processor can be configured to stimulate electrically and/or acoustically according to the transfer function of the signal processor. In some examples, the type of stimulation used can depend on the input signal received by the signal processor. For instance, in an exemplary embodiment, the frequency content of the input signal to the signal processor can dictate the type of stimulation. In some cases, frequencies below a threshold frequency could be represented using one of electrical and acoustic stimulation while frequencies above the threshold frequency could be represented using the other of electrical and acoustic stimulation. Such a threshold frequency could be adjustable based on the hearing profile of the patient. Using a limited range of frequencies can reduce the number of frequency domains, and thus the number of contact electrodes, on the cochlear electrode. In other examples, rather than a single threshold frequency defining which frequencies are stimulated electrically and acoustically, various frequencies can be stimulated both electrically and acoustically. In some such examples, the relative amount of electrical and acoustic stimulation can be frequency-dependent. As described elsewhere herein, the signal processor transfer function can be updated to meet the needs of the patient, including the electrical and acoustic stimulation profiles.

Additionally or alternatively, while many examples show a middle ear sensor being in communication with an implanted signal processor, in various embodiments, one or more additional or alternative input sources can be included. For instance, in some embodiments, a microphone can be implanted under a user's skin and can be placed in communication with the signal processor (e.g., via a detachable connector such as 171). The signal processor can receive input signals from the implanted microphone and provide signals to the stimulator based on the received input signal and the signal processor transfer function. Additionally or alternatively, systems can include a middle ear sensor as an input source, wherein the middle ear sensor is configured to detect stimuli (e.g., pressure signals) from the wearer's inner ear (e.g., within the cochlear tissue).

With further reference to FIGS. 1 and 4, in some examples, a system can include a shut-off controller 104, which can be configured to wirelessly stop an electrical stimulator 130 from stimulating the patient's cochlear tissue and/or an acoustic stimulator 150 from stimulating the patient's ossicular chain. For example, if the system is malfunctioning or an uncomfortably loud input sound causes an undesirable level of stimulation, the user may use the shut-off controller 104 to cease stimulation from the stimulator 130. The shut-off controller 104 can be embodied in a variety of ways. For example, in some embodiments, the shut-off controller 104 can be integrated into other external components, such as the programmer 100. In some such examples, the programmer 100 includes a user interface by which a user can select an emergency shut-off feature to cease stimulation. Additionally or alternatively, the shut-off controller 104 can be embodied as a separate component. This can be useful in situations in which the patient may not have immediate access to the programmer 100. For example, the shut-off controller 104 can be implemented as a wearable component that the patient can wear at all or most times, such as a ring, bracelet, necklace, or the like.

The shut-off controller 104 can communicate with the system in order to stop stimulation in a variety of ways. In some examples, the shut-off controller 104 comprises a magnet that is detectable by a sensor (e.g., a Hall-Effect sensor) implanted in the patient, such as in the processor and/or the implantable battery and/or communication module 140. In some such embodiments, when the magnet is brought sufficiently close to the sensor, the system can stop stimulation of the cochlear tissue or ossicular chain.

After the shut-off controller 104 is used to disable stimulation, stimulation can be re-enabled in one or more of a variety of ways. For example, in some embodiments, stimulation is re-enabled after a predetermined amount of time after it had been disabled. In other examples, the shut-off controller 104 can be used to re-enable stimulation. In some such examples, the patient brings the shut-off controller 104 within a first distance of a sensor (e.g., a magnetic sensor) to disable stimulation, and then removes the shut-off controller 104. Subsequently, once the patient brings the shut-off controller 104 within a second distance of the sensor, stimulation can be re-enabled. In various embodiments, the first distance can be less than the second distance, equal to the second distance, or greater than the second distance. In still further embodiments, another device such as a separate turn-on controller (not shown) or the programmer 100 can be used to re-enable stimulation. Any combination of such re-enabling of stimulation can be used, such as alternatively using either the programmer 100 or the shut-off controller 104 to enable stimulation or combining a minimum "off" time before any other methods can be used to re-enable stimulation.

In some embodiments, rather than entirely disable stimulation, other actions can be taken, such as reducing the magnitude of stimulation. For example, in some embodiments, the shut-off sensor can be used to reduce the signal output by a predetermined amount (e.g., absolute amount, percentage, etc.). In other examples, the shut-off sensor can affect the transfer function of the signal processor to reduce the magnitude of stimulation in a customized way, such as according to frequency or other parameter of an input signal (e.g., from the middle ear sensor).

In some examples, implantable battery and/or communication module can be used to provide power and/or data (e.g., processing instructions) to other system components via lead 190. Different challenges exist for communicating electrical signals through a patient's body. For example, safety standards can limit the amount of current that can safely flow through a patient's body (particularly DC current). Additionally, the patient's body can act as an undesired signal path from component to component (e.g., via contact with the housing or "can" of each component).

Figure 5:
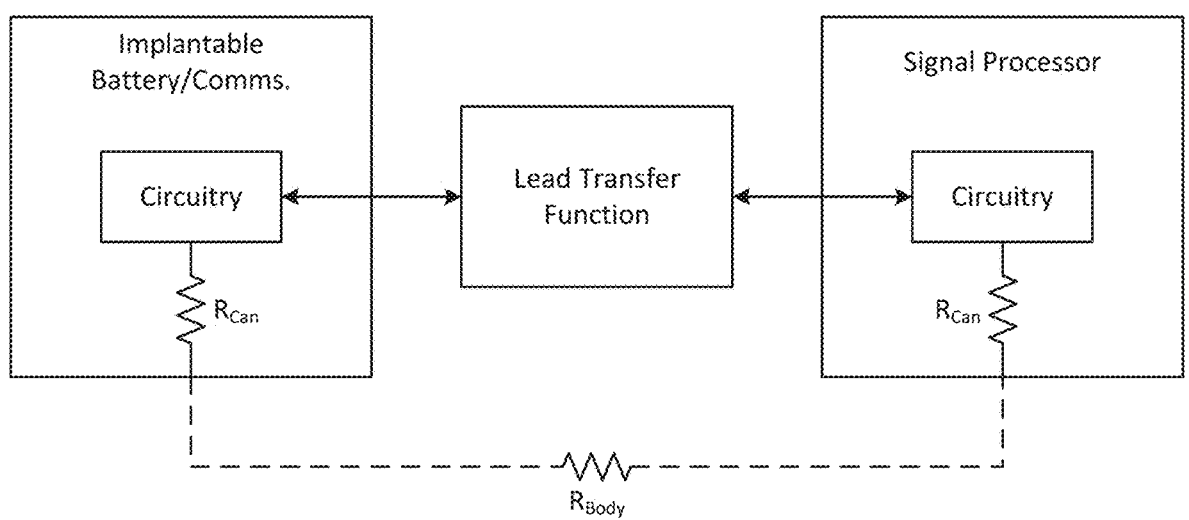
FIG. 5 s a high level electrical schematic showing communication between the implantable battery and/or communication module and the signal processor.

FIG. 5 is a high-level electrical schematic showing communication between the implantable battery and/or communication module and the signal processor. In the illustrated embodiment, the implantable battery and/or communication module includes circuitry in communication with circuitry in the signal processor. Communication between the circuitry in the implantable battery and/or communication module and the signal processor can be facilitated by a lead (190), represented by the lead transfer function. The lead transfer function can include, for example, parasitic resistances and capacitances between the leads connecting the implantable battery and/or communication module and the signal processor and the patient's body and/or between two or more conductors that make up the lead (e.g., 191). Signals communicated from the circuitry of the implantable battery and/or communication module to the circuitry in the signal processor can include electrical power provided to operate and/or stimulate system components (e.g., the middle ear sensor, signal processor, electrical and/or acoustic stimulator, and/or cochlear electrode) and/or data (e.g., processing data regarding the transfer function of the signal processor).

Various systems and methods can be employed provide communication between system components. Some examples of possible communication techniques are described in PCT patent application No. PCT/US20/19166, which is incorporated by reference. In some examples, data can be communicated to the implantable battery and/or communication module from an external component, such as a programmer as shown in FIG. 1. In an exemplary process, a programmer, such as a clinician's computer, can be used to communicate with a patient's fully implanted system via the implantable battery and/or communication module, which can communicate information to other system components, such as via lead 190.

During such processes, a clinician can communicate with the signal processor, and, in some cases, with other components via the signal processor. For example, the clinician can cause the signal processor to actuate an electrical and/or an acoustic stimulator in various ways, such as using various electrical stimulation parameters, combinations of active contact electrodes, various acoustic stimulation parameters, and various combinations thereof. Varying the stimulation parameters in real time can allow the clinician and patient to determine effectiveness of different stimulation techniques for the individual patient. Similarly, the clinician can communicate with the signal processor to update transfer function. For example, the clinician can repeatedly update the transfer function signal processor while testing the efficacy of each one on the individual patient. In some examples, combinations of stimulation parameters and signal processor transfer functions can be tested for customized system behavior for the individual patient.

In some embodiments, various internal properties of the system may be tested. For instance, various impedance values, such as a sensor impedance or a stimulator impedance can be tested such as described in U.S. Patent Publication No. 2015/0256945, entitled TRANSDUCER IMPEDANCE MEASUREMENT FOR HEARING AID, which is assigned to the assignee of the instant application, the relevant portions of which are incorporated by reference herein.

As described elsewhere herein, in various embodiments, the processor generally receives an input signal, processes the signal, and generates a stimulation signal, which can be applied via an integrated stimulator or a separate stimulator in communication with the processor (e.g., as shown in FIGS. 1 and 4). In some such embodiments, the input signal received via the signal processor is generated by an implantable sensor, such as a middle ear sensor.

However, such sensors often measure or otherwise receive some stimulus that is converted into an output that is read and processed by the signal processor. For example, some middle ear sensors may produce a different output signal for a given stimulus depending on a variety of factors, such as variability in a wearer's inner-ear anatomy and motion. Thus, the output of a sensor for a given input may be not predictable while designing a system, especially across a range of frequencies.

Figure 6B:
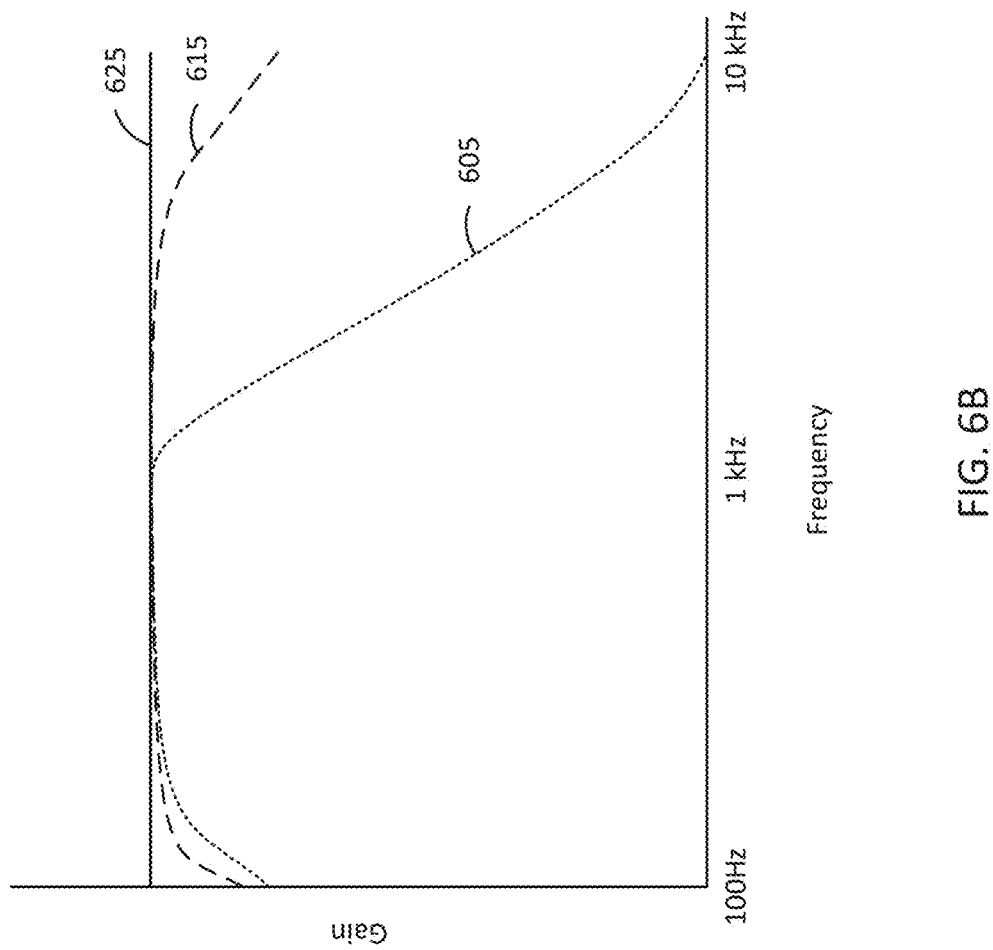
FIG. 6B shows an exemplary gain vs. frequency response curve for signals at various stages in the processing configuration.
Figure 6A:
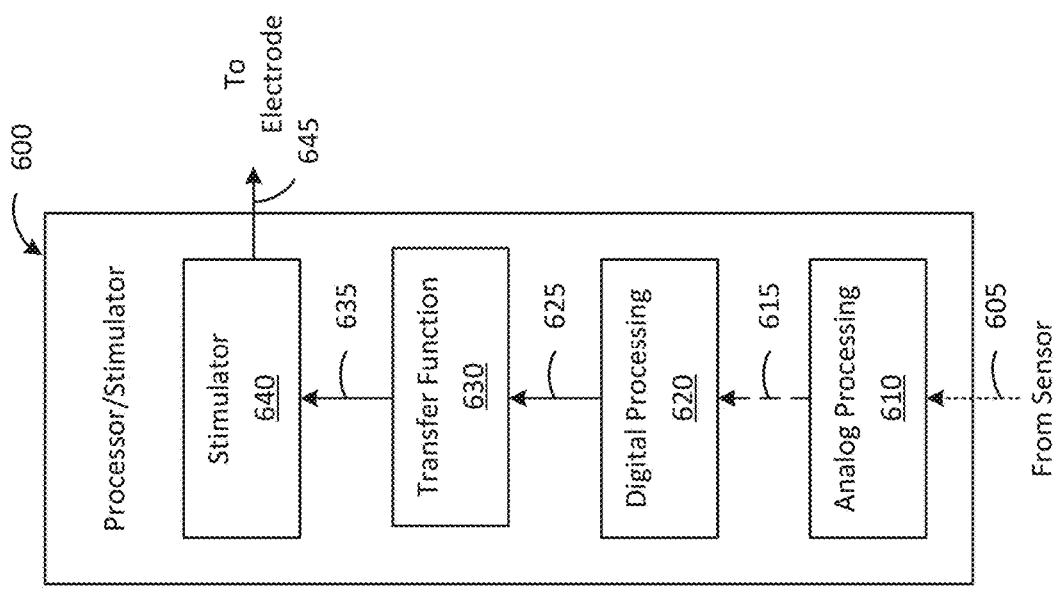
FIG. 6A is a schematic diagram showing an exemplary signal processing configuration for adapting to variability in a sensor frequency response.

FIG. 6A is a schematic diagram showing an exemplary signal processing configuration for normalizing a stimulus signal and adapting to variability in a sensor frequency response. FIG. 6B shows an exemplary gain vs. frequency response curve for signals at various stages in the processing configuration. "Gain" associated with a particular frequency, as used with respect to FIG. 6B, refers to a relationship (e.g., a ratio) between the magnitude of an input stimulus received by the sensor and processor and the magnitude of the resulting signal at various stages of processing. In the illustrated example, the processor/stimulator 600 receives an input signal 605 from the sensor.

As shown in FIG. 6B, the gain is very uneven over the distribution of frequencies shown in the plot. For instance, according to the illustrated example, a stimulus signal received at the sensor at 1 kHz will result in a much larger magnitude in signal 605 compared to a stimulus signal of the same magnitude received at the sensor at 10 kHz. Such a discrepancy in frequency response can make signal processing difficult. Moreover, such frequency response in general may vary from person to person, or over the course of a wearer's lifetime due to physical movement of a sensor or anatomical changes.

The input signal 605 undergoes analog processing 610 to produce an analog processed signal 615. As shown in FIG. 6B, the analog processing step 610 improves the consistency of the gain across the range of frequencies, as the analog processed signal 615 provides a flatter frequency response curve than does the input signal 605. In some embodiments, the analog processing can include one or more filter and/or amplifiers generally configured to flatten out the frequency response curve as shown in FIG. 6B. In some examples, the analog processing components 610 within the processor/stimulator 600 can be substantially the same across various implantable systems in order to provide a first order correction of the frequency response. In other examples, an analog processing configuration 610 can be customized to the wearer, for example, based on known anatomical features, measurements, analysis, or the like.

The analog processed signal 615 undergoes a digital processing step 620 to produce a digitally processed signal 625. As shown in FIG. 6B, the digital processing step 620 further improves the consistency of the gain across the range of frequencies, as the digitally processed signal 625 provides a flatter frequency response curve than does the analog processed signal 615. In some embodiments, the digital processing 620 can be configured to substantially flatten the frequency response to correct remaining frequency response inconsistencies in the analog processed signal 615. For instance, in some embodiments, after digital processing 620, a stimulus signal of a given magnitude at a first frequency and a second frequency will result in a digitally processed signal 625 having the same magnitude at the first and the second frequencies. Thus, the digitally processed signal 625 corresponds to a normalized stimulus signal, reducing or eliminating the variability that comes with different wearer anatomies and wearer motion and/or changes over time. Having a normalized frequency response across large frequency ranges can simplify assessment of the efficacy of the implanted system, programming a signal processor transfer function, assessing system operation, and the like. In some examples, a flat frequency response can enable the system to present an electrical stimulus to the wearer at appropriate intensity levels, for example, with respect to received external acoustic stimuli, independent of the frequency content of the external acoustic stimuli.

In some embodiments, the digital processing 620 can be customized via a calibration process after the system has been implanted. In an exemplary calibration process, a clinician or other user may provide a series of stimulus signals, for instance, at a plurality of frequencies and having like amplitudes, to be "picked up" by the sensor, which generates an input signal 605 for each received signal. The clinician or other user may then sample the resulting analog processed signal 615 and/or an initial digitally processed signal 625 at the plurality of frequencies to determine the remaining non-uniformity in gain across the frequency sweep. The digital processing 620 can be either established or updated to compensate for non-uniformities in order to establish a substantially flat frequency response curve in the digitally processed signal 625. In some examples, a plurality of signals having different frequencies are provided in sequence and a magnitude response (e.g., gain) at each frequency is determined. After determining such a magnitude response, the digital processing stage 620 can be updated based on the response vs. frequency relationship in order to flatten the frequency response curve.

In an alternate process, a white noise signal can be provided to be "picked up" by the sensor. A transform (e.g., a Fast Fourier Transform, or FFT) of the signal can be performed in order to extract the frequency content of the signal. The extracted frequency content can used to determine a magnitude response at each frequency and the digital processing 620 can be updated to flatten the frequency response similar to described above.

In the illustrated example of FIG. 6A, the digitally processed signal 625 (e.g., having a uniform gain across a frequency range with respect to input signals received from the sensor) is processed according to the signal processor transfer function 630 to generate a stimulation signal 635. Stimulation signal 635 can be received by the stimulator 640, which can apply an electrical signal 645 to the electrode such as described elsewhere herein.

In some examples, the digital processing step 620 to provide a uniform frequency response can be incorporated into the transfer function 630 wherein the analog processed signal 615 is digitally processed to both flatten the frequency response and to generate a stimulation signal (e.g., 635) according to a programmed transfer function. Additionally or alternatively, as described elsewhere herein, in some examples, stimulator 640 can be located external to the processor rather than being combined as a single processor/stimulator component 600.

As described elsewhere herein, while many examples show a middle ear sensor being in communication with an implanted signal processor, in various embodiments, one or more additional or alternative input sources can be included. For instance, in some embodiments, a microphone can be implanted under a user's skin and can be placed in communication with the signal processor (e.g., via a detachable connector such as 171). The signal processor can receive input signals from the implanted microphone and provide signals to the stimulator based on the received input signal and the signal processor transfer function.

Figure 7:
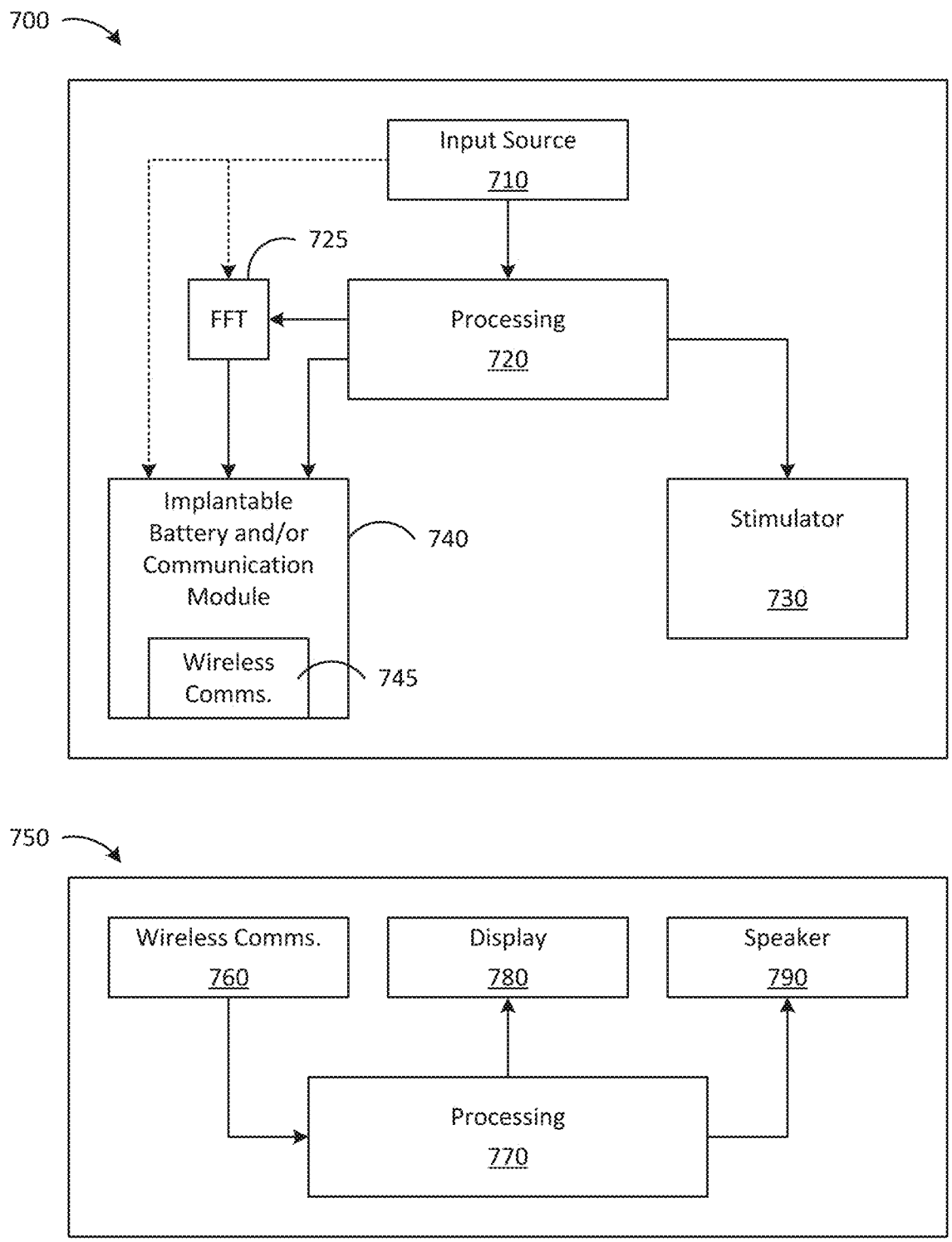
FIG. 7 is a schematic diagram of an example cochlear implant and analysis system include an exemplary implantable cochlear implant system and an external device.

FIG. 7 shows a schematic diagram of an example cochlear implant and analysis system including an exemplary implantable cochlear implant system 700 and an external device 750. The implantable cochlear implant system 700 includes an input source 710, such as a microphone, middle ear sensor, inner ear sensor, or the like, in communication with processing stage 720 which in some embodiments comprises the signal processor (e.g., signal processor 120). In some examples, steps performed within the processing stage 720 are performed entirely within the signal processor (e.g., 120). In other examples, processing stage 720 can include one or more additional processing components other than the signal processor to perform one or more additional or alternative processing functions.

The input source 710 can be a sensor configured to receive an input representative of ambient sound and generate an input signal representative of the received input. For example, as described elsewhere herein, the input source 710 can be an inner ear sensor, middle ear sensor, microphone, or other sensor which can receive sound and generate a representative input signal.

In the example of FIG. 7, the processing stage 720 is in communication with a stimulator 730. As described elsewhere herein, processing stage 720 can receive an input signal from the input source 710 and can output a stimulation signal to the stimulator 730. Processing stage 720 is further in communication with an implantable battery and/or communication module 740. Power and/or data can be sent between the processing stage 720 and the implantable battery and/or communication module 740. In some examples, the implantable battery and/or communication module 740 sends power to the processing stage 720 and the processing stage 720 sends data to the implantable battery and/or communication module 740. In some examples, the implantable battery and/or communication module 740 sends both power and data to the processing stage 720.

As described, the illustrated processing stage 720 can be representative of any element or combination of elements which can receive an input signal from input source and generate an output signal based on the input signal. For example, processing stage 720 can be a signal processor which receives the input signal generated by input source 710 and can generate a stimulation signal based on the received input signal. In some examples, the stimulation signal can be based on the input signal received by processing stage 720 and on a transfer function. As described elsewhere herein, the stimulator 730 can receive the stimulation signal and can apply an electrical signal to an electrode. In some examples, processing includes one or more intermediate steps used to generate the stimulation signal based on a signal received from input source 710. For instance, as described elsewhere herein, in some examples, one so ore such intermediate steps include analog processing, digital processing, and/or generating a stimulation signal via a transfer function as described with respect to FIGS. 6A and 6B. Each of the intermediate steps performed by processing stage 720 can generate an intermediate signal.

In some examples, the cochlear implant system 700 can be configured to output one or more signals, such as an input signal from input source 710, a stimulation signal, and/or one or more intermediate signals, to an external device 750, for example, via a wireless communication interface 745.

In the illustrated example, wireless communication interface 745 is included in implantable battery and/or communication module. As shown and described elsewhere herein, processing stage 720 is in communication with an implantable battery and/or communication module 740, and signals (e.g., power and/or data) can travel between processing stage 720 and the implantable battery and/or communication module 740. For instance, in some examples, processing stage 720 can generate a stimulation signal and send the stimulation signal to the implantable battery and/or communication module 740. Additionally or alternatively, processing stage 720 can send an intermediate signal to the implantable battery and/or communication module.

In an example process, processing stage 720 can receive an input signal from input source 710, perform an analog processing step on the input signal, and output the resulting signal (an analog processed signal) to the implantable battery and/or communication module 740. Further, in some examples, the processing stage 720 does not perform any processing on the input signal and sends the input signal to the implantable battery and/or communication module 740. Additionally or alternatively, in some embodiments, the input source 710 can be in direct communication with the implantable battery and/or communication module 740 in order to provide an input signal thereto. In general, any signal present within the processing stage 720 (e.g., a signal received for processing, one or more intermediate signals during processing, or a signal resulting from the processing) can be directed to the implantable battery and/or communication module 740.

In the example of FIG. 7, the implantable battery and/or communication module 740 is configured to communicate with the external device 750 through the wireless communication interface 745. In some such examples, the implantable battery and/or communication module 740 can send the one or more received signals, such as an input signal, an intermediate signal, and/or a stimulation signal, to the external device 750 using the wireless communication interface 745. Additionally, in some examples, the wireless communication interface 745 can receive signals from the external device 750 and send those signals to the processing stage 720.

In an example embodiment, implantable battery and/or communication module 740 receives a command from external device 750 designating a signal for analysis via wireless communication interfaces 760, 745. The implantable battery and/or communication module 740 can relay a command to the processing stage 720 identifying the first signal for analysis. The processing stage 720 can generate an analysis signal such as described elsewhere herein and communicate to the implantable battery and/or communication module that the signal is available. The implantable battery and/or communication module can be configured to read the signal from the processing stage 720 and wirelessly communicate a representation of the signal to the external device 750.

As described elsewhere herein, the implantable cochlear implant system can be utilized to provide improved hearing to a wearer. However, it can be helpful to analyze the system to ensure its proper operation. As described, with respect to the example of FIG. 7, the implantable cochlear implant system 700 can output various signals generated within the system to the external device 750 for analysis and/or further operations. In some embodiments, the processing stage 720, which can be a signal processor (e.g., signal processor 120), is configured to receive an analysis input indicating a first signal for analysis. Such first signal can include any signal within the processing steps of processing stage 720, such as in input signal, intermediate signal, or a stimulation signal.

In some embodiments, the analysis input, indicating a first signal for analysis, is sent by the external device 750 to the cochlear implant system 700, for example, via implantable battery and/or communication module 740. In some embodiments, the implantable battery and/or communication module 740 can determine the first signal from the received analysis input and request such signal from the processing stage 720. In other examples, the implantable battery and/or communication module 740 can communicate the analysis input to the processing stage 720 and the processing stage can determine the first signal and output the signal to the implantable battery and/or communication module 740.

As described elsewhere herein, in some examples, the first signal for analysis comprises an input signal received from the input source 710. Alternatively, in some examples, the first signal for analysis comprises intermediate signals which can be the result of one or more processing steps performed by the processing stage 720. The one or more processing steps can be intermediate steps such as analog processing, digital processing, and/or transforming via a transfer function. For example, the signal 625 produced after digital processing 620 in FIG. 6A can be an intermediate signal. Further, in some examples, the first signal for analysis can be a stimulation signal, such as the stimulation signal generated by the processing stage 720. In some such examples, the first signal for analysis is the same stimulation signal that can be sent to the stimulator 730 to stimulate an electrode.

In some embodiments, the processing stage 720 is configured to generate an analysis signal based on the received analysis input. The analysis signal can comprise a representation of the first signal indicated by the analysis input. For example, the analysis signal can comprise an exact representation of the first signal. However, in some examples the analysis signal can comprise a modified representation of the first, such as through downsampling the first signal. In such an example, the analysis signal carries less information than the first signal and can require less processing power to be manipulated, sent, and/or received.

Accordingly, the cochlear implant system 700 can be configured to generate an analysis signal representative of the first signal identified by the analysis input. In various examples, the analysis signal can include the first signal itself or a downsampled version thereof.

In some embodiments, the processing stage 720 outputs the analysis signal to the wireless communication interface 745 for communication to an external device 750. As described, in some examples, the wireless communication interface 745 is positioned within the implantable battery and/or communication module 740. In other examples, wireless communication interface 745 of the cochlear implant system 700 can be positioned in an alternate location of the system, such as within a signal processor (e.g., within processing stage 720) or as a standalone component.

In some embodiments, one or more illustrated components of the cochlear implant system 700 can be included in a single implanted housing. For example, in some embodiments, as described elsewhere herein, a signal processor and stimulator can be included in a single housing. In some examples, wireless communication interface 745 can be included within the same housing that includes both the processor and stimulator. Additionally, in some examples, such a housing can further include a battery (e.g., implantable battery and/or communication module 740) for providing electrical power to the signal processor and the stimulator. Similarly, in some embodiments, input source 710, such as a microphone, can be included within the housing, such as via a microphone integrated with the signal processor as described elsewhere herein.

In FIG. 7, the wireless communication interface 745 communicates wirelessly with a wireless communication interface 760 of the external device 750. The wireless communication interfaces 745, 760 can include communication via a variety of communication protocols, such as Wi-Fi, Bluetooth, NFC or other data transmission protocols. In some example operations, the wireless communication interface 745 of the cochlear implant system 700 can output a second signal representative of the analysis signal to the external device 750, such as a downsampled version of the analysis signal or other variation thereof to facilitate wireless communication The external device 750 includes a wireless communication interface 760, processing stage 770, a display 780, and a speaker 790. Processing stage 770 can include one or more digital signal processor, one or more microprocessors, microcontrollers, application specific integrated circuits (ASICs) or the like. In some examples, the external device 750 comprises only one of the display 780 and the speaker 790. In some examples, the external device 750 does not include a display or speaker, however, in some such examples, a display and/or speaker can be in communication with the external device 750.

In various examples, the external device can be any device or series of devices that can receive signals from the implantable cochlear implant system 700 through a wireless communication interface. For example, the external device can be a computer, smartphone, tablet, or the like with a processor and a wireless communication interface (e.g. Bluetooth) and a built-in or external speaker and/or display. In some examples, the external device can comprise a user interface which can allow user inputs.

In the example of FIG. 7, the processing stage 770 of the external device 750 is in communication with the wireless communication interface 760 and can receive and process signals received by the wireless communication interface 760. For example, in some embodiments, the wireless communication interface 760 can receive a second signal representative of an analysis signal from the wireless communication interface 745 of the implantable cochlear implant system. Processing stage 770 can receive the second signal and generate a representation of the analysis signal.

The representation of the analysis signal can include the received second signal or changes thereto such as arithmetic changes and other mathematical manipulation. For example, processing stage 770 can downsample or transform the received second signal. Downsampling the analysis can reduce the complexity of the signal, thereby reducing the processing power required to manipulate, send, and receive an ultimate representation of the analysis signal. Transforming the signal can be used to extract and/or display one or more aspects of the second signal, such as the frequency content thereof or the like.

In some examples, processing stage 770 can receive the second signal and output a representation of the analysis signal to various devices (e.g. a display 780 and/or speaker 790). In some such examples, processing stage 770 can manipulate the second signal into a format such that the various devices can use the second signal. For example, processing stage 770 can manipulate the second signal into a format such that the display 780 can visually display the second signal or other representation of the analysis signal and/or so that speaker 790 can output an audio representation of the analysis signal.

Continuing with the example of FIG. 7, external device 750 includes the display 780 in communication with processing stage 770. In some examples, the display 780 is separate from external device 750, but is in communication with the external device 750. Display 780 can be any type of display (e.g. LCD, LED) and can include computer monitors, televisions, and handheld device displays. In operation, display 780 can display a visual representation of any received signals. For example, the display can display a visual representation of the analysis signal (e.g., based on the signal received by processing stage 770).

As described, the analysis signal can include any of a variety of signals present in the cochlear implant system 700, such as an input signal, intermediate signal, or stimulation signal. Accordingly, in some embodiments, the display can display a representation of any such signals. For example, the display 780 can display a visual representation of an input signal generated by the input source, which is representative of ambient sound. In some examples, such a display can include a visual representation of the ambient sound for facilitating visual comparison the input signal and the ambient sound causing the input signal. An operator can readily see any discrepancies between the two visual representations and, in some examples, can adjust the system to correct for the discrepancies.

The external device 750 of FIG. 7 also includes a speaker 790 in communication with processing stage 770. In some examples, speaker 790 is separate from external device 750, but is in communication with the external device 750. Speaker 790 can be any type of speaker which produces audio output. Speaker 790 can produce audio outputs representative of any signals which it receives.

In some examples, speaker 790 receives signals from processing stage 770 and generates an audio output based on the received signals. In some examples, processing stage 770 outputs a signal to the speaker to cause the speaker to output an audio representation of the analysis signal. This can allow an operator to "hear" a representation of the analysis signal via speaker 790.

As described, the analysis signal can include any of a variety of signals present in the cochlear implant system 700, such as an input signal, intermediate signal, or stimulation signal. Thus, in some embodiments, the speaker 790 can output an audio representation of any of the intermediate signals, such as those produced by processing stage 720, into audible outputs.

In an example operation of the overall cochlear implant system of FIG. 7, a desired first signal is the input signal generated by the input source 710. External device 750 can communicate the desired first signal to the cochlear implant system 700 via an analysis input designating the input signal, for example, in response to a received user input. Input source 710 generates an input signal representative of a received input (e.g. a pure tone or ambient sound). Processing stage 720 can be configured to generate and output an analysis signal representative of the input signal, such as a downsampled version thereof or the input signal itself. The processing stage can output the analysis signal to the wireless communication interface 745 of the implantable battery and/or communication module 740. In some examples, the implantable battery and/or communication module can be configured to receive the input signal directly from the input source, bypassing the processing stage 720.

The cochlear implant system can be configured to output a second signal representative of the input signal via wireless communication interface 745 to an external device 750. The second signal representative of the input signal can be sent to processing stage 770 which can generate an audio and/or visual output representative of the input signal for output via speaker 790 and/or display 780. The output representation (e.g., visual and/or audio) of the input signal can be used to analyze, for example, the operation of the input source 710. For instance, in an example embodiment, external device 750 can be configured to output a display representative of the input signal as well as a display representative of the audio signal received by the input source to generate the input signal. Such representations can be compared to assess operation of the input source.

The cochlear implant system 700 of FIG. 7 includes a transform stage 725 that can be configured to transform a signal into a transformed signal. In some examples, the transform stage 725 is configured to perform a transform, such as a fast Fourier transform, to convert a signal into a frequency domain representation thereof. While shown for illustrative purposes as being outside of the processing stage 720, in some embodiments, transformations performed by the transform stage 725 are performed by the same component(s) implementing functions of the processing stage 720 (e.g., signal processor 120).

As described elsewhere herein, in various examples, the first signal represented by the analysis signal can include any of a variety of signals, such as the input signal, a resulting stimulation signal, or an intermediate signal used in creating the stimulation signal. In some examples, the analysis signal comprises the first signal or a downsampled version thereof. However, in some embodiments, the analysis signal can include a transformation of an identified first signal, such as a transformation into a frequency domain representation of the first signal.

In an example embodiment, the cochlear implant system 700 receives an analysis input identifying a first signal for analysis. The cochlear implant system 700 can be configured to generate an analysis signal representative of the first signal by transforming the first signal via the transform stage 725. For instance, in an example embodiment, the identified first signal for analysis is the stimulation signal generated by processing stage 720 and output to stimulator 730, and the analysis signal representative thereof comprises a fast Fourier transform of the stimulation signal comprising the frequency content thereof. The cochlear implant system can be configured to output a second signal representative of such analysis signal to the external device 750, for example, for subsequent analysis of the frequency content of the stimulation signal by a user.

While transform stage 725 is described above as applying a fast Fourier transform, in some examples, different transformations that result in an output signal comprising a frequency domain representation of the input signal can be used, such as a standard Fourier transform, a discrete Fourier transform, or other appropriate transform. In some embodiments, the transformation stage can be configured to transform a first signal into a frequency domain in squared units (e.g., $V^2$ per frequency bin), and such squared units can be communicated to the external device. The external device can be configured to convert the received signal into appropriate units for analysis and/or display.

In general, using transform stage 725 to transform the first signal into a frequency domain representation can enable the cochlear implant system to communicate data more efficiently. In some examples, transform stage 725 sample a signal for transformation (e.g., an input signal, an intermediate signal, etc.) for a predetermined period of time to generate the analysis signal. For instance, in some examples, the transform stage 725 can sample a first signal for an amount of time between 20 milliseconds and two seconds and perform a transformation (e.g., an FFT) on the sampled signal to generate the transformed signal representing the first signal. he transformed data can include data representing the entire span of time the signal was sampled, but can itself be a smaller data set when compared to transmitting the original signal for the entire duration of sampling. Thus, transforming the signal can enable the cochlear implant system to efficiently output a signal representative of the first signal to the external device. In some embodiments, transforming the signal can include averaging a transformed signal over several windows of time. For example, in some embodiments, transform stage 725 is configured to calculate a FFT of a desired signal over a predetermined time window. The transform stage 725 can calculate a plurality of FFTs of the signal over a corresponding plurality of time windows and average the FFTs in order to reduce the impact of random noise present in the signal.

Figure 8:
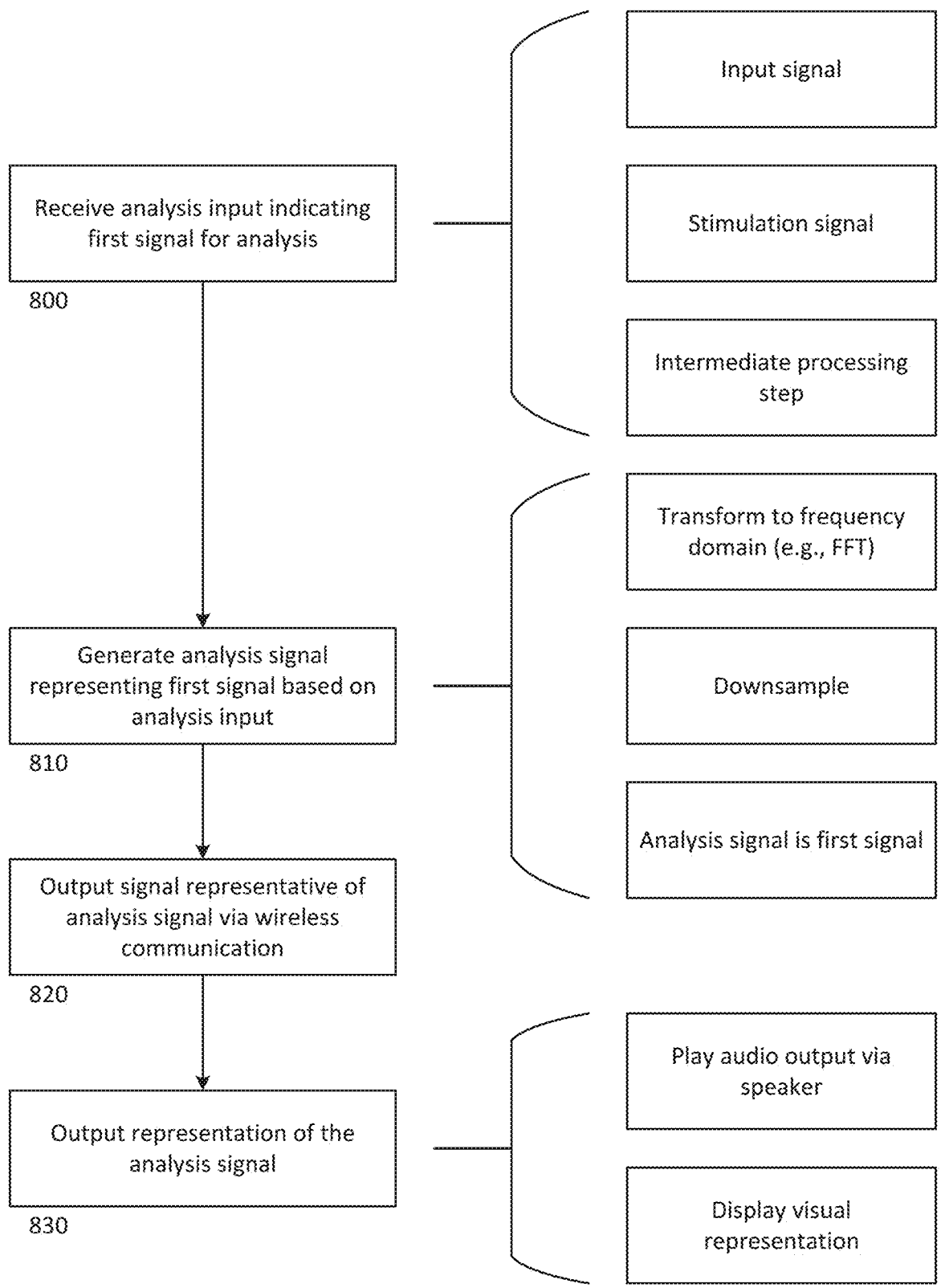
FIG. 8 is a flow diagram including example operations of a cochlear implant and analysis system according to an aspect of the present disclosure.

Moving to FIG. 8, FIG. 8 is a flow diagram including example operations of a cochlear implant and analysis system according an aspect of the present disclosure. Starting with step 800, the system receives an analysis input indicating a first signal for analysis. In some examples, processing (e.g. a signal processor) receives the analysis input indicating a first signal for analysis. In some examples, a signal processor receives the analysis input indicating a first signal for analysis. The first signal for analysis can be any signal within the cochlear implant and analysis system. In some examples, the first signal can be an input signal received from an input source. In some examples, the first signal can be a stimulation signal output by a signal processor. Further, in some examples, the first signal can be an intermediate processing step such as an output of a digital or analog processing stage of a signal processor. Once the analysis input has been received, which indicates the first signal for analysis, the operation can continue with step 810.

In step 810 of the example of FIG. 8, an analysis signal representing the first signal for analysis is generated based on the analysis input. In some examples, a processing stage (e.g. signal processor) generates the analysis signal based on the indicated first signal. As shown in FIG. 8, generating the analysis signal can include various changes to the first signal for analysis. For example, in order to generate an analysis signal, the first signal for analysis can be transformed to the frequency domain whereby the analysis signal comprises a frequency domain representation of the first signal. In some examples, the transformation to the frequency domain is achieved by applying a fast Fourier transform to the first signal. In further examples, a fast Fourier transform is applied to a sample of the first signal to generate an analysis signal. The sample of the first signal can be any length, but in some examples, the sample is between 20 milliseconds and two seconds in length.

Additionally or alternatively, in some examples, generating an analysis signal representative of the first signal comprises downsampling the first signal. Downsampling can include reducing the number of samples of a signal such that the new signal has fewer entries and/or less information than the original signal. In some examples, downsampling can include compressing the first signal to generate the analysis signal. It can be advantageous to downsample the first signal as the resulting signal (e.g. the analysis signal) can require fewer processing resources including processing and storage in memory (e.g. hard disk drive, solid state drive).

While generating the analysis signal can comprise of applying a fast Fourier transform or downsampling, it will be appreciated that other changes to the first signal for generating the analysis signal are contemplated (e.g. other mathematical operations). Further, in some examples, more than one change can be applied to the first signal to generate the analysis signal. For example, applying a fast Fourier transform to the first signal and downsampling the result of the fast Fourier transform. In some embodiments, as seen in FIG. 8, generating the analysis signal can include not changing the first signal. In such embodiments, the generated analysis signal is the first signal. For example, in some embodiments, the cochlear implant system can be configured to stream the first signal from the system to an external device.

Once the analysis signal, representing the first signal and based on the analysis input, is generated in step 810, the operation can continue with step 820. In step 820 a signal (e.g. a second signal) representative of the analysis signal is output via wireless communication. The output signal can be the analysis signal or a modified signal representative thereof, such as a downsampled representation of the analysis signal. In some examples, the wireless communication is performed via a wireless communication interface. In some examples the signal representative of the analysis signal is output to an external device via the wireless communication. As described elsewhere herein, the external device can include wireless communication (e.g. a wireless communication interface), a display, a speaker, and a processing stage. In some examples, the processing stage can process the representation of the analysis signal. For example, the processing stage can adapt the signal for output on a display.

In step 830 of the operation of the system, the external device can output a representation of the analysis signal. As shown in the example of FIG. 8, outputting the representation of the analysis signal can include playing the representation of the analysis signal via a speaker. The output representation of the analysis signal, in such a case, comprises an audio output representative of the analysis signal which the speaker can play. For example, as discussed elsewhere herein, in some examples, the analysis signal representative of a first signal can be representative of a stimulation signal sent to the stimulator. In such examples, outputting the representation of the analysis signal via a speaker can include outputting an acoustic representation of the stimulation signal via the speaker. In some examples, more than one speaker can be used. For instance, in some embodiments, audio representations of a plurality of analysis signals can be output via a corresponding plurality of speakers. In other examples, audio representations of a plurality of analysis signals can be combined into a single audio output.

Additionally or alternatively, as shown in FIG. 8, outputting the representation of the analysis signal can include visually displaying a representation of the analysis signal, such as via a display of an external device. For example, as discussed elsewhere herein, in some examples, the analysis signal can be a transformation of the first signal to the frequency domain. As the first signal can be an input signal, the analysis signal can be a transformation of the input signal into the frequency domain. In such examples, the signal representative of the analysis signal, which itself includes information representative of the frequency content of the input signal, is output to the display. Thus, the display can display a visual representation of the analysis signal, which, in some examples, is representative of the frequency content of the input signal received from the input source. In some examples, more than one display can be used. For instance, in some embodiments, visual displays representative of a plurality of analysis signals can be presented via a corresponding plurality of displays.

The example of FIG. 8 illustrates many different combinations for operation of the cochlear and analysis system. For example, step 800 indicates that an input signal, a stimulation signal, or other signals such as those from intermediate processing steps, can be used in the operation. Step 810 provides multiple options for manipulating the signal from step 800 such as transforming the signal to the frequency domain, downsampling the signal, or simply continuing with the same signal. Once the signal is output via wireless communication, the output can be processed and/or output further to a speaker and/or a display. The various combinations are not necessarily limited to combinations of individual elements. For example, the representation of the analysis signal can include both playing audio output via a speaker and displaying a visual representation. In another example, generating an analysis signal can comprise applying a fast Fourier transform to the first signal and downsampling the transformed signal or vice versa.

The various examples in FIG. 8 can be combined in various ways as will be understood by a person skilled in the art. For example, in some examples, a stimulation signal can be downsampled and a visual representation thereof can be output. Additionally or alternatively, a signal at an intermediate processing step can be transformed to a frequency domain, and an audio output representative thereof can be output via a speaker. Various combinations are possible.

Figure 9:
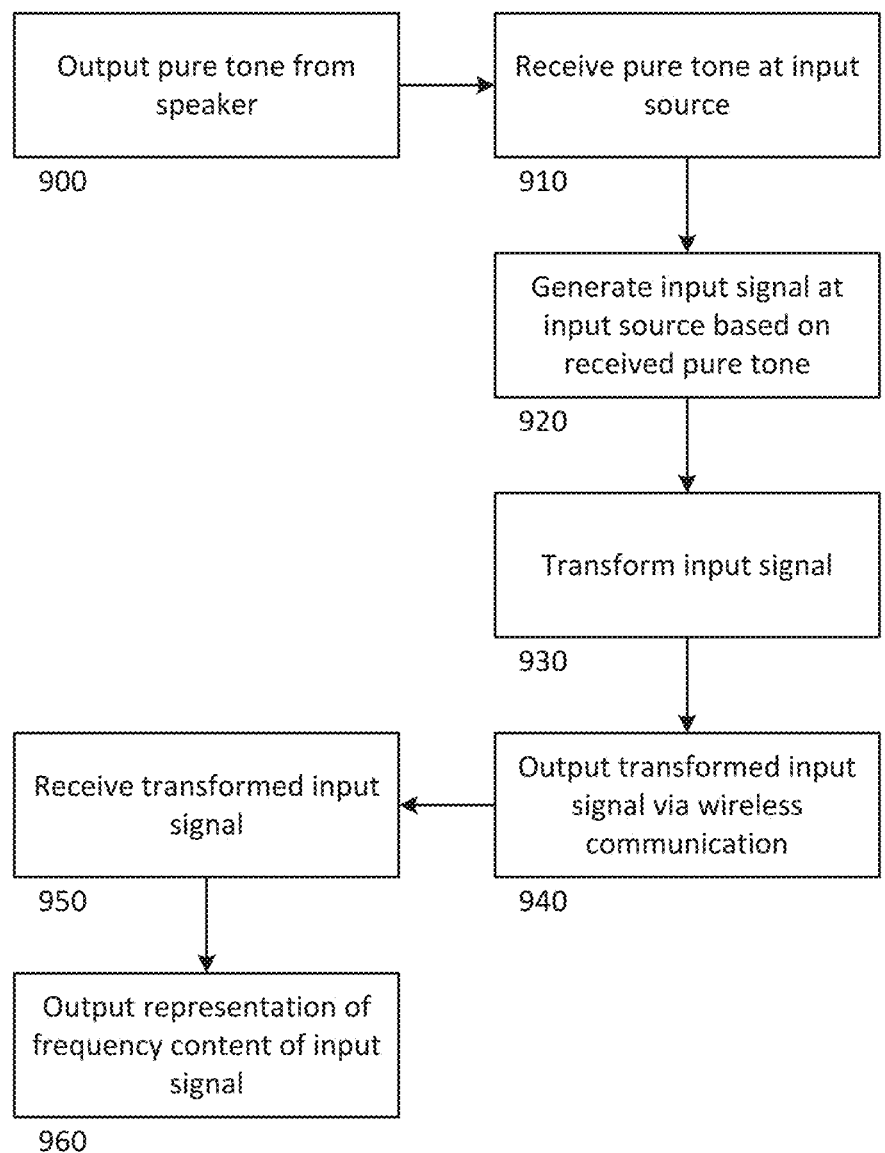
FIG. 9 is an example operation of an example cochlear implant and analysis system.

FIG. 9 shows example operation of an example cochlear implant and analysis system. The operation begins in step 900 whereby a speaker outputs a pure tone. The pure tone can have any frequency, phase, and amplitude. In some examples, the speaker is the same speaker of the external device (e.g. 790 of FIG. 7). In step 910, an input source (e.g. microphone, middle ear sensor) receives the pure tone. Once the pure tone is received, the input source can generate an input signal based on the received pure tone as in step 920. Further, in step 930, the input signal is transformed. In some examples, a signal processor transforms the input signal. In some embodiments, the transformation is an application of the fast Fourier transform to the input signal, which transforms the input signal into the frequency domain. The transformed input signal is then output in step 940 via wireless communication. In some examples, the transformed signal is output to an external device via the wireless communication. In some embodiments, the wireless communication is a wireless communication interface. Once output, the transformed input signal is received as in step 950, a representation of the received, transformed input signal can be output as shown in step 960. The representation of the received, transformed input signal is a representation of the frequency content of the input signal. In some examples, the representation of the received transformed input signal is output to a speaker and/or a visual display as described elsewhere herein.

In some examples, a physician, such as an audiologist, can monitor aspects of cochlear implant system operation of the example of FIG. 9. An audiologist can initiate outputting a pure tone from a speaker as in step 900. The audiologist can monitor the cochlear implant and analysis system and aurally and/or visually compare the pure tone output by the speaker and the output representation of the frequency content of the input signal generated in the process of FIG. 9. In this way, the audiologist can more easily determine if the implantable cochlear implant system is operating desirably or if one or more aspects of the system needs adjustment, repair, or replacement. In some examples, the audiologist can visually compare the output representation of the frequency content of the input signal to a known pure tone (e.g. 1 kHz sine wave) on a display. In some examples, the audiologist can aurally compare the output representation of the frequency content of the input signal to a known pure tone (e.g. 1 kHz sine wave) via listening to a speaker play the pure tone and then playing the output representation. The operation in FIG. 9 is also advantageous as the system outputs the representation of the frequency content of the input signal wirelessly. Wireless transmission of the signals can decrease noise which may corrupt or otherwise inadvertently change the signals.

The example operation of FIG. 9 can be repeated and can include using multiple different pure tones. Using multiple different pure tones can allow the system to be operated across a wide range of frequencies. Operating across a wide range of frequencies can help determine if the output representation of the frequency content of the input signal is consistent across such frequencies. For instance, during an example operating, a first pure tone of 1 kHz can be used in the process of FIG. 9. The resulting output representation of the frequency content can include a pure 1 kHz signal. A second pure tone of 2 kHz can then be used in the process of FIG. 9 with the resulting output representation of the frequency content including representations of a 2 kHz signal and a harmonic signal at 6 kHz. Thus, inconsistencies of the input source operation can be detected by analyzing a representation of the frequency content of the input signal in the presence of a known stimulus (e.g., a pure tone emitted from a speaker). Such practices can be used to diagnose operating problems within a cochlear implant system, such as testing operating of the input source at a plurality of frequencies.

It can be desirable to minimize harmonics within the system and operation of the cochlear implant and analysis system (e.g. FIG. 9) can aid in determining if harmonics are present in any signals in the system. In some examples, odd harmonics (e.g. $3^{rd}$, $5^{th}$) are more undesirable than even harmonics (e.g. $2^{nd}$, $4^{th}$) and the system can aid in determining if odd or even harmonics are present. For example, as in FIG. 9, operation of the system can include transforming an input signal received from an input source to the frequency domain and outputting a representation of the transformed input signal. The representation of the transformed signal can depict the frequencies generated by the system, which can include harmonics present within the signal. The representation of the transformed signal can thus be used to check the output of the input source (e.g. sensor) and determine if the sensor is operating desirably.

While the example operation of FIG. 9 illustrates sequential steps, in some example operations, one or more steps are performed in parallel. For instance, in some examples, a first pure tone can be output from a speaker for a period of time (e.g., 0.5-2 seconds). After the first pure tone stops playing from the speaker, the cochlear implant and analysis system can perform the operations of FIG. 9. However, before the representation of the frequency content of the input signal is output, the speaker can output a second pure tone which can then be processed by the system. In this way, operation of the system for multiple different pure tones can be shortened. In some such examples, representations of the input signal resulting from each of a plurality of pure tone stimuli can be presented simultaneously or sequentially.

In some examples, some steps of the process shown FIG. 9 can be performed using portable or take-home, for example, for use by a user in a home setting. In some examples, a take-home system can be configured to output a pure tone from a speaker at step 900. The implanted system can perform steps 910-940. In some examples, the transformed input signal is output to an external device, which can send the signal or a representation thereof to a clinical setting for analysis by a clinician (e.g., via the internet). Such an arrangement allows a wearer to initiate a system diagnostic process at home and communicate the results to a clinician for further analysis.

Figure 10:
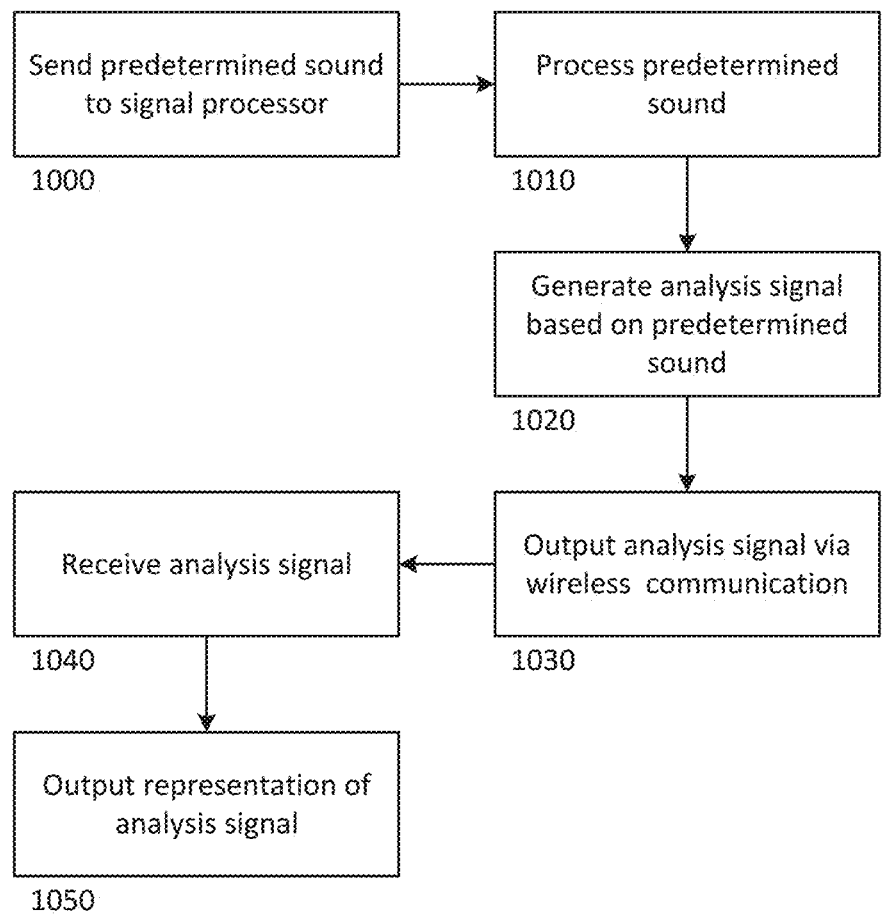
FIG. 10 is an example operation of an example cochlear implant and analysis system.

FIG. 10 shows another example operation of an example cochlear implant and analysis system. In the process of FIG. 10, a predetermined sound is sent to a signal processor in step 1000. In some embodiments, sending the predetermined sound to the signal processor comprises using an external device configured to output the predetermined sound via a speaker of the external device. An input source (e.g., a microphone or middle ear sensor) can receive the predetermined sound and generate an input signal which can include a representation of the predetermined sound and can be received by the signal processor. In contrast, in some embodiments, the input source does not receive the predetermined sound, but instead, the predetermined sound is directly sent to the signal processor, for example, via wireless communication from an external device. Such predetermined sound can be used to bypass the input source and provide the signal processor with a predetermined signal.

In step 1010, the predetermined sound is processed. Processing the predetermined sound can include applying a programmed transfer function thereto to generate a stimulation signal. Additionally or alternatively, as described elsewhere herein, in some embodiments, processing the predetermined sound includes performing an analog processing step and/or a digital processing step as described with respect to FIGS. 6A and 6B. The process of FIG. 10 further includes generating an analysis signal in step 1020. As described elsewhere herein, in some embodiments, the analysis signal can include, for example, a transformed (e.g., via FFT) or downsampled representation of a signal, such as a signal resulting from the processing in step 1010. Accordingly, in some examples, the analysis signal can include a downsampled representation of a result of an analog processing step (e.g., 610 in FIG. 6). In other examples, the analysis signal can include a stimulation signal for output to the stimulator. As described herein, various examples of analysis signals are contemplated The analysis signal is then output via wireless communication in step 1030. In step 1040, the analysis signal is received, for example, via an external device. As described, in some examples, an external device receives the analysis signal via wireless communication. A representation of the analysis signal is then output in step 1050, for example, via a speaker and/or a display as described herein.

In some examples, similar to described with respect to FIG. 9, some of the process shown FIG. 10 can be performed by a user in a home setting. In some examples, an external device can send one or more predetermined sounds to the signal processor at step 1000. The implanted system can perform steps 1010-1030. In some examples, the analysis signal is output to an external device, which can send the signal or a representation thereof to a clinical setting for analysis by a clinician (e.g., via the internet). Such an arrangement allows a wearer to initiate a system diagnostic process at home and communicate the results to a clinician for further analysis.

After outputting a representation of a signal as in steps 960 and 1050, various analysis can be performed. For example, an audiologist can find a noise floor of various frequencies by observing the output representations of the signal based on inputs with specific frequencies. In another example, the output representation of the signal is representative of a stimulation signal sent to a stimulator of a patient. The output representation can be output to a speaker and an audiologist can listen to it and compare it to the input signal.

In some examples, some such processes allow the implant system to function like a spectrum analyzer. For instance, a process similar to that in FIG. 9 can allow for analyzing a frequency response of the implanted system to one or more input stimuli to the system. Such analysis can be used to determine if there is a problem with one or more implanted components. For example, such a process can be used to determine whether the sensor output accurately reflects the frequency content of a received stimulus.

In some examples, a frequency response of the system can be indicative of one or more clinical conditions, such as a fluid buildup within the ear. Such buildup can affect operation of a sensor in identifiable ways that can assist in diagnosing such a condition. In some cases, determining a cause of system operation issues, for example, due to fluid buildup or the like, can assist in determining any necessary intervention for improving system operation. Such determination can help a clinician determine a best course of action for addressing any undesirable operation of the system. This can reduce the likelihood of performing more invasive or high-risk procedures as a diagnostic or empirical attempt at resolving system issues. Instead, such procedures can be performed after diagnostic processes or other analyses described herein suggest such procedures are necessary.

In some examples, various processes described herein, such as example operations of FIG. 9 and FIG. 10 can be performed prior to the implantable cochlear implant system being implanted within a patient (e.g. during manufacturing) to ensure system components are working properly. Such operations can be performed after the implantable cochlear implant system is implanted within the patient, for example, after first implanting the system components to ensure proper functionality, during routine check-up or maintenance procedures, and/or for troubleshooting in the event system operation issues arise. Operation of the cochlear implant and analysis system can be advantageous compared to other cochlear implant systems as it is possible to perform the operation without lab test equipment. Thus, operation of the system can be done in non-lab settings, require fewer resources, and can be an inexpensive way to test the implantable cochlear implant system.

Various non-limiting embodiments have been described. These and others are within the scope of the following claims.

The invention claimed is:

1. A cochlear implant and analysis system comprising:
an external device comprising a display; and
an implantable cochlear implant system comprising:
a stimulator configured to provide electrical stimulation;
an input source configured to receive an input representative of ambient sound and generate an input signal representative of the received input;
a signal processor in communication with the stimulator and the input source, the signal processor being programmed with a transfer function and wherein the signal processor outputs a stimulation signal to the stimulator based on the input signal received from the input source and the transfer function; and
a wireless communication interface in communication with the external device; and wherein
the signal processor is configured to:
receive an analysis input indicating a first signal for analysis, the first signal comprising the input signal or a result of one or more processing steps performed by the signal processor;
generate an analysis signal based on the received analysis input, the analysis signal comprising a representation of the first signal; and output the analysis signal to the wireless communication interface;

the wireless communication interface is configured to output a second signal representative of the analysis signal to the external device; and the external device is configured to receive the second signal from the wireless communication interface of the implantable cochlear implant system and output a representation of the analysis signal, outputting the representation of the analysis signal comprising displaying a visual representation of the analysis signal on the display.

2. The cochlear implant and analysis system of claim 1, wherein the stimulator, the signal processor, and the wireless communication interface are included in a single housing.

3. The cochlear implant and analysis system of claim 1, further comprising an implantable battery and/or communication module in communication with the signal processor and including the wireless communication interface, and wherein the signal processor is configured to output the analysis signal to the implantable battery and/or communication module.

4. The cochlear implant and analysis system of claim 1, wherein the generating the analysis signal comprises transforming the first signal so that the analysis signal comprises a frequency domain representation of the first signal.

5. The cochlear implant and analysis system of claim 4, wherein transforming the first signal comprises applying a Fast Fourier Transform to the first signal.

6. The cochlear implant and analysis system of claim 5, wherein the applying the Fast Fourier Transform to the first signal comprises applying a Fast Fourier Transform of a sample of the first signal between 20 milliseconds and 2 seconds in length.

7. The cochlear implant and analysis system of claim 4, wherein the first signal comprises the input signal received from the input source.

8. The cochlear implant and analysis system of claim 4, wherein the first signal comprises the stimulation signal.

9. The cochlear implant and analysis system of claim 1, wherein the analysis signal comprises the first signal.

10. The cochlear implant and analysis system of claim 1, wherein outputting the second signal comprises streaming the analysis signal from the wireless communication interface to the external device.

11. The cochlear implant and analysis system of claim 1, wherein the first signal comprises the input signal received from the input source;

the generating the analysis signal comprises transforming the first signal into a frequency domain so that the analysis signal is representative of frequency content of the input signal received from the input source; and wherein the displaying the visual representation of the analysis signal on the display comprises displaying information representative of the frequency content of the input signal received from the input source.

12. The cochlear implant and analysis system of claim 1, wherein the external device comprises a speaker.

13. The cochlear implant and analysis system of claim 12, wherein the output representation of the analysis signal comprises an audio output representative of the analysis signal.

14. The cochlear implant and analysis system of claim 13, wherein:

the first signal comprises the stimulation signal; and the audio output representative of the analysis signal is representative of the stimulation signal.

15. The cochlear implant and analysis system of claim 12, wherein the external device is configured to output a predetermined sound via the speaker, and wherein the input signal generated by the input source includes a representation of the predetermined sound.

16. The cochlear implant and analysis system of claim 15, wherein the predetermined sound comprises a pure tone sound.

17. The cochlear implant and analysis system of claim 16, wherein:

the first signal comprises the input signal received from the input source;

the generating the analysis signal comprises transforming the first signal into a frequency domain so that the analysis signal is representative of frequency content of the input signal received from the input source; and the outputting the representation of the analysis signal comprises displaying information representative of the frequency content of the input signal received from the input source on the display.

18. The cochlear implant and analysis system of claim 17, wherein the outputting the representation of the analysis signal further comprises displaying information representative of the frequency content of the pure tone sound output via the speaker of the external device.

19. The cochlear implant and analysis system of claim 1, wherein the received analysis input indicating the first signal for analysis comprises a signal received from the external device.

20. The cochlear implant and analysis system of claim 19, wherein the external device comprises a user interface and is configured to:

receive a user input identifying the first signal; and output a wireless command signal designating the first signal based on the received user input.

21. The cochlear implant and analysis system of claim 1, wherein the signal processor is further configured to:

receive a predetermined sound from the external device via the wireless communication interface; and generate a second stimulation signal based on the received predetermined sound and the transfer function and not based on an input signal received from the input source.

22. The cochlear implant and analysis system of claim 1, wherein the first signal comprises an output of a digital processing stage or an analog processing stage of the signal processor.

* * * * *